(12) United States Patent
Knight

(10) Patent No.: US 7,904,313 B2
(45) Date of Patent: Mar. 8, 2011

(54) RECRUITING A PATIENT INTO A CLINICAL TRIAL

(75) Inventor: Stephen C. Knight, Cambridge, MA (US)

(73) Assignee: Quintiles, Inc., Durham, NC (US)

( * ) Notice: Subject to any disclaimer, the term of this patent is extended or adjusted under 35 U.S.C. 154(b) by 1245 days.

(21) Appl. No.: 09/938,295

(22) Filed: Aug. 23, 2001

(65) Prior Publication Data

US 2002/0099570 A1 Jul. 25, 2002

Related U.S. Application Data

(60) Provisional application No. 60/227,484, filed on Aug. 24, 2000.

(51) Int. Cl.
*G06F 19/00* (2006.01)
*G06F 15/16* (2006.01)

(52) U.S. Cl. .................................. 705/3; 726/11; 705/2

(58) Field of Classification Search .................... None
See application file for complete search history.

(56) References Cited

U.S. PATENT DOCUMENTS

| | | | |
|---|---|---|---|
| 5,734,883 A | 3/1998 | Umen et al. | 395/601 |
| 5,991,731 A | 11/1999 | Colon et al. | 705/3 |
| 6,014,631 A * | 1/2000 | Teagarden et al. | 705/3 |
| 6,196,970 B1 | 3/2001 | Brown | |
| 6,839,678 B1 * | 1/2005 | Schmidt et al. | 705/3 |
| 7,251,609 B1 | 7/2007 | McAlindon et al. | |
| 2001/0034631 A1 | 10/2001 | Kiselik | 705/8 |
| 2002/0002247 A1 | 1/2002 | Allcock et al. | 705/3 |
| 2002/0002474 A1 * | 1/2002 | Michelson et al. | 705/3 |
| 2006/0229916 A1 * | 10/2006 | Michelson et al. | 705/2 |

FOREIGN PATENT DOCUMENTS

| | | |
|---|---|---|
| EP | 0 936 566 | 8/1999 |
| WO | WO 98 39720 | 9/1998 |
| WO | WO 98 49647 | 11/1998 |
| WO | WO 01 55942 | 8/2001 |
| WO | WO 01/55942 A1 | 8/2001 |
| WO | WO 01/93160 * | 12/2001 |
| WO | WO 0193160 A1 * | 12/2001 |

OTHER PUBLICATIONS

ReSearch Clinical Services Signs Exclusive Agreement With Healthdemographics.
Advance Paradigm Announces Interactive Web Site; Features Secure, Convenient Member Access to Pharmacy Benefit Management and Information Services.
Quintiles Invests in Physicians' Online, the Leading Online Service for Doctors.
Object Products, Inc. to Demonstrate Clinical Trials Patient Recruitment Solution at HIMSS.
Keratoconus patients recruited via Web.
American Oncology Resources Launches First System to Match Cancer.

(Continued)

*Primary Examiner* — Luke Gilligan
*Assistant Examiner* — Rachel L Porter
(74) *Attorney, Agent, or Firm* — Scott E. Kamholz; Foley Hoag LLP

(57) ABSTRACT

Techniques are described for recruiting a patient into a clinical trial, including receiving patient-specific data from a remote network device at a server, accessing criteria of more than one clinical trial at the server, and determining one or more clinical trials having criteria satisfied by the patient-specific data.

22 Claims, 31 Drawing Sheets

OTHER PUBLICATIONS

Hospital Web Site Earns Physician Respect With Clinical Trials Section.

Internet (Clinical Trials) New Software Means Paperless Clinical Trials, Quicker Cures.

CenterWatch Launches Service to Help Patients Access NIH Clinical Trials.

DrugMonitor.com Launches Web Site to Advance Clinical Trial Participation.

drhoop.com & Quinines Launch Service to Recruit Clinical Trial Patients on the Internet; Quintile-drkoop.com Clinical Trials Information Center Expands Awareness and Availability of Clinical Trials as a Treatment Option for Consumers; Service Harnesses Power of the Internet to Accelerate Enrollment of Qualified Patients, Increasing Speed and Efficiency of Drug Development Process; Center is First Consumer On-Line Service With Interactive Pre-Screening, Enrollment Tracking Features.

America's Doctor to Begin Clinical Trials Program.

drkoop.com "Clinical Trials" web site (17 pages).

Centerwatch.com "CenterWatch Patient Notification Service" web site (2 pages).

"TVisions Wins Top Web Extranet Award; Recognized for Creative, Life-Saving Site," *Business Wire*, Jul. 1, 1999, [online] [retrieved on Aug. 27, 2007]. Retrieved from the Internet<URL: http://findarticles.com/p/articles/mi_m0EIN/is_1999_July_1/ai_55042198/print>.

* cited by examiner

FIG. 3

Clinical Trial Search – Lung Cancer print this    email this

Instructions

Answer the questions below to search our Trials Database. Your answers will be used to find trials that match your needs--the more questions you answer, the better the match will be. All information that you enter will remain strictly confidential.
(Read our privacy policy for more details.)

There are currently 102 trials recruiting for Lung Cancer.

Please Enter Your Date of Birth (mm/dd/yyyy): _____ ← 402

◉  Enter a ZIP code  [02142]

Enter how far, in miles, you would be
   willing to travel from this ZIP code to    [500]     } ← 404
   participate in a trial (up to 999).

OR

○  In which state would you like to search for a trial?  [Show All Locations ▼]
                                                          Alabama
                                                          Alaska
                                                          Arizona Which of the      [Lung Cancer – Small Cell (SCLC)  ▼]    ← 408
following
conditions
do you have?

Clinical Trials
Find Clinical Trials
About Clinical Trials

Investigational Treatments
Overview
Drugs in Development

Current Treatments
Overview
Current Drugs

Basic Disease Information
Introduction
Overview
FAQs
Additional Resources

Viewpoint
Current Edition
Archives

Keyword Search:  _____ go

Help  Advanced

FIG. 4

Step 1 of 3: Register with Veritas Medicine

Clinical Trials
Find Clinical Trials
About Clinical Trials

Investigational Treatments
Overview
Drugs in Development

Current Treatments
Overview
Current Drugs

Basic Disease Information
Introduction
Overview
FAQs
Additional Resources

Viewpoint
Current Edition
Archives

Keyword Search: go

Help Advanced

Create a username & password

Username: ⎱ 1102
Password (min. 6 digits):
Confirm Password: ⎱ 1104
Email:
Confirm Email:

☐ Yes, I'd like to receive the bi-weekly Viewpoint for Lung Cancer.
☐ Yes, I'd like to subscribe to Personalized Trial Matching for Lung Cancer.

In the event that you lose your password:
the following question and answer will allow you to regain access to your account.

Select a question...
Type your answer here: ⎱ 1108 submit

Register using our secure server
Unsure? Click here for more information.

Veritas Medicine Features

- Already registered?
  Please login here.

- Save trial information & articles
  in your own personal files.

- Receive e-mail updates
  of your choice, on new clinical trials, drug and treatment information.

- Contact specific clinical trials
  to enroll in a trial, or gather more specific information.

log in now

FIG. 11

Veritas Internet Content Editor

Lung Cancer — Select a disease go to the Lung Cancer front page

Lung Cancer Text items ← 1602

- Treatment Overviews, Trial Questionnaire related content, Weekly updates

Lung Cancer Drug and Drug Class Information

- View/Edit all Lung Cancer drugs
- Drug Class and drug details
- Drug and drug class reference articles
- Web links - related to drugs, drug classes, or the disease
- Results to Date

Lung Cancer Trial Information

- My Clinical Trials questionnaire builder ← 1604
- Trial detail information - edit trials, trial locations, and match trials to questionnaire questions.
- Unmatched Trials
- Patient Test-Drive ← 1608

Other Lung Cancer content items

- FAQ questions
- Conferences
- MD Editor Info

Questions? Comments? Problems? email tech@veritasmedicine.com.

Veritas Internet Content Editor

Select a disease go to the Lung Cancer front page

Return to the questionnaire preview page

Add a new question to Lung Cancer, level 2

This question type allows the user to select MORE THAN ONE answer from a list of multiple options.

Enter Question Text _____ ← 2002

Question Options check to
               make default    ☐ no default option.

Option 1     ○    _____
Option 2     ○    _____
Option 3     ○    _____    } 2004
Option 4     ○    _____
Option 5     ○    _____

Submit Question

FIG. 20

Veritas Internet Content Editor

Add a new trial  Search for a specific trial

Lung Cancer Trials available for editing – 124 trials found. Trials 1 thru 20 shown.

Click on a title to edit trial information, or select an action from the drop-down menu next to the title.

| Submit Date | Trial ID | Protocol ID | Title | VM Client | Action | Approved? |
|---|---|---|---|---|---|---|
| 10/25/2000 | 501322 | | 10-Propargyl-10-Deazaaminopterin in Treating Patients With Stage IIIB or Stage IV Non-small Cell Lung Cancer | No client assigned | Please Select ▼ | X |
| 06/11/2001 | 106680 | | BBR 3464 in Treating Patients With Metastatic Small Cell Lung Cancer That Has Not Responded to Previous Treatment | Government Trial | Please Select ▼ | X |
| 08/08/2000 | 1958 | | Budesonide in Treating Former and Current Smokers With Bronchial Dysplasia | No client assigned | Please Select ▼ | X |
| 06/11/2001 | 106732 | | Capecitabine in Treating Patients With Malignant Mesothelioma | Government Trial | Please Select ▼ | X |
| 06/11/2001 | 1840 | | Carboplatin, Paclitaxel, and Radiation Therapy With or Without Thalidomide in Treating Patients With Stage III Non-small | Government Trial | Please Select ▼ | X |

Select a disease go to the Lung Cancer front page

Clinical Trials Matching Questionnaire: Lung Cancer

Trial.- " BBR 3464 in Treating Patients With Metastatic Small Cell Lung Cancer That Has Not Responded to Previous Treatment " ← 2302

Select the box next to a question to indicate you want to match the trial against that question Level 1 Questions ☑  1. Which of the following conditions do you have?
       ↑
      2304        2308

| Inclusion Criterion ▼ |
|---|
| ☐ Lung Cancer -- Non-Small Cell (NSCLC) |
| ☑ Lung Cancer -- Small Cell (SCLC) |
| ☐ Lung Cancer -- Malignant pleural mesothelioma (MPM) |
| ☐ None - Current/Former smoker |
| ☐ I do not know. |

2310

} 2312

☑  2. Select the appropriate stage and type of cancer:

| Inclusion Criterion ▼ |
|---|
| ☐ NSCLC: Stage IA/IB |
| ☐ NSCLC: Stage IIA/IIB |
| ☐ NSCLC: Stage IIIA/IIIB |
| ☐ NSCLC: Stage IIIB (with malignant effusion)/Stage IV/Recurrent |
| ☐ SCLC: Limited Stage (confined to one lung) |
| ☐ SCLC: Extensive Stage (spread outside one affected lung) |
| ☑ SCLC: Recurrent |
| ☐ MPM: Localized (confined to one side of the chest) |
| ☐ MPM: Extensive (spread beyond one lung) |
| ☐ MPM: Recurrent |
| ☐ none |
| ☐ I do not know. |

[Continue Matching]

FIG. 23

Veritas Internet Content Editor

My Clinical Trials Questionnaire: Lung Cancer

Answer following Questions:

1. Which of the following conditions do you have? ← 2502

○ Lung Cancer -- Non-Small Cell (NSCLC)  ○ Lung Cancer -- Small Cell (SCLC)  ○ Lung Cancer -- Malignant pleural mesothelioma (MPM)  ○ None - Current/Former smoker  ⊙ I do not know.

2. Select the appropriate stage and type of cancer:

○ Stage IIA/IIB  ○ NSCLC: Stage IIIA/IIIB  ○ NSCLC: Stage IA/IB  ○ NSCLC: effusion)/Stage IV/Recurrent  ○ SCLC: Limited Stage (confined to one lung)  ○ NSCLC: Stage IIIB (with malignant  SCLC: Extensive Stage (spread outside one affected lung)  ○ SCLC: Recurrent  ○ MPM: Localized (confined to one side of the chest)  ○ none  ⊙ MPM: Extensive (spread beyond one lung)  ○ MPM: Recurrent  ○ I do not know.

[Submit] [Go Back]

Select a disease ▼ go to the Lung Cancer front page

FIG. 25

Veritas Internet Content Editor

Select a disease go to the Lung Cancer front page

← 2508

2504

(TRIAL ID:1835) Inhaled Doxorubicin in Treating Patients With Primary Lung Cancer or Lung Metastases
[ Question3: ? Question4: ? Question5: Yes Question6: ? Question7: ? Question8: Ignore Question9: ? Question10: ? ]
Percentage: 3 / 4: 75% ← 2510
Show Trial? YES (TRIAL ID:1842) Vaccine Therapy Plus QS21 in Treating Patients With Small Cell Lung Cancer That Has Responded to Initial Therapy
[ Question3: Yes Question4: ? Question5: ? Question6: No Question7: Ignore Question8: Ignore Question9: ? Question10: ? ]
Percentage: 4 / 6: 67%
Show Trial? NO (TRIAL ID:1914) Marimastat Following Chemotherapy in Treating Patients With Small Cell Lung Cancer
[ Question3: ? Question4: ? Question5: ? Question6: ? Question7: ? Question8: Ignore Question9: ? Question10: ? ]
Percentage: 4 / 4: 100%
Show Trial? YES (TRIAL ID:1936)
[ Question3: Yes Question4: ? Question5: ? Question6: ? Question7: ? Question8: Ignore Question9: ? Question10: ? ]
Percentage: 4 / 5: 80%
Show Trial? YES (TRIAL ID:1949) Depsipeptide to Treat Lung Cancer
[ Question3: ? Question4: ? Question5: ? Question6: Yes Question7: ? Question8: Ignore Question9: ? Question10: ? ]
Percentage: 2 / 4: 50%
Show Trial? YES (TRIAL ID:1953) Irinotecan Plus Gemcitabine in Treating Patients With Unresectable or Metastatic Solid Tumors
[ Question3: Yes Question4: ? Question5: ? Question6: ? Question7: ? Question8: Ignore Question9: ? Question10: ? ]
Percentage: 4 / 5: 80%
Show Trial? YES (TRIAL ID:1956) Combination Chemotherapy Plus Peripheral Stem Cell Transplantation in Treating Patients With Metastatic Cancer.

Breast Cancer find clinical trials | FAQ | resources | search

Veritas Medicine
FOR PATIENTS

Select a disease about us
contact us
home

My Clinical Trials

2802

New Drugs
You have potentially matched against 1 New Drug trial(s).

| Contact Name | Telephone | Email |
|---|---|---|
| Michael Benjamin Atkins, Principal Investigator | (617) 667-4599 | info@veritasmedicine.com |

Existing Drug Combinations
You have potentially matched against 3 Drug Combination trial(s) based on the information you provided on the My Clinical Trials form. Click on a drug name below to view trial details.

| Drug Name | Location | City/State |
|---|---|---|
| Doxorubicin, Cyclophosphamide, Docetaxel | New England Medical Center Hospital | Boston, MA |
| Doxorubicin, Cyclophosphamide, Paclitaxel, Docetaxel | Beth Israel Deaconess Medical Center | Boston, MA |
| Raloxifene and Tamoxifen | Baystate Medical Center | Springfield, MA |

- My Clinical Trials
- Learn more about clinical trials

Breast Cancer home

FIG. 28

RECRUITING A PATIENT INTO A CLINICAL TRIAL

CROSS REFERENCE TO RELATED APPLICATION

This application claims the benefit of priority from U.S. Provisional Patent Application Serial No. 60/227,484, filed Aug. 24, 2000, the entire disclosure of which is incorporated herein by reference.

BACKGROUND

Drug development is a slow and expensive process, with the ultimate step of clinical trials representing one of the costliest and riskiest steps. For a drug to be approved in most countries, particularly the United States, it must pass through a rigorous process of human testing to determine dosage, adverse effects, and efficacy. Only one in ten drugs which commence clinical trials in the U.S. eventually receive approval for human use. The annual cost of conducting clinical trials in the United States is more than 7.4 billion dollars, representing nearly 33% of all R&D expenditures.

One of the slowest and riskiest steps in the clinical trial process itself is the initial enrollment (or recruitment) of patients in the trial. There are approximately 1,000 drugs in Phase II/III trials in the US at any given time, with 1,400 worldwide. Recruitment in clinical trials takes an average of 40 weeks to complete, with 40-50% of the patients screened ultimately deemed inappropriate. It has been estimated that the number of patients needed for clinical trials is doubling every 5 years. Recent drug discovery technologies such as genomics, combinatorial chemistry, and high throughput screening will tend to exacerbate such a need. In a trial, patients must be matched against strict enrollment parameters to ensure proper evaluation of clinical endpoints in the correct patient population. Patients who are inappropriately enrolled for a particular clinical trial present two problems: an improper skewing of adverse effects, dosage, and efficacy; and a slowing of the clinical trial process itself since more patients must be enrolled as the inappropriate patients are ultimately weeded out.

While the Internet and the World Wide Web can facilitate the rapid and global exchange of vast amounts of information, the very nature of such a networked system implicates security concerns, particularly when sensitive information such as patient health records or proprietary drug trial information could be compromised. Nevertheless, the increased availability of medical information on the Internet has resulted in a public eager to try cutting-edge therapies when traditional methods have failed or when no therapy has been approved, as witnessed by the plethora of web sites related to AIDS and cancer information. However, current methods for clinical trial recruitment, including Internet sites dedicated to providing some clinical trial information, have been inefficient. The FDA Modernization Act of 1997 requires pharmaceutical companies to submit trial information to a national registry to promote public access to clinical trials, yet pharmaceutical outfits are unwilling to post sensitive proprietary clinical trial information on the Internet due to competitive or security concerns. An estimated 30% of the ongoing Phase II/III clinical trials ongoing are proprietary for pharmaceutical companies, with 10% of the trials completely confidential, 10% of the trials having confidential inclusion/exclusion criteria, and 10% having confidential site locations. Each pharmaceutical site thus posts only a small percentage of all clinical trials available, often leaving the patient or clinician to perform an exhaustive and often futile search. Patients and clinicians with limited resources or time constraints would hesitate to undertake such searches, particularly given the incomplete offerings at many sites.

SUMMARY

In an embodiment, a system for recruiting a patient into a clinical trial comprises a patient interface; a set of patient-specific data, collected from the patient through the patient interface; a set of trial-specific criteria corresponding to the clinical trial; a content interface; a set of disease-specific data, collected from a disease expert through the content interface; and instructions for matching, including instructions for coupling the set of patient-specific data to the disease-specific data and producing a set of patient-disease characteristics, and instructions for coupling the set of patient-disease characteristics to the set of trial-specific criteria and determining whether a match exists between the patient and the clinical trial.

In an embodiment, the patient interface comprises an HTML-encoded web page.

In an embodiment, a system for recruiting a patient into a clinical trial further comprises a patient database, including the patient-specific data.

In an embodiment, a system for recruiting a patient into a clinical trial further comprises a clinical trial database, including the set of trial-specific criteria.

In an embodiment, a system for recruiting a patient into a clinical trial further comprises a disease database, including the set of disease-specific data.

In an embodiment, the patient-specific data, the disease-specific data, the trial-specific criteria, the instructions for matching, and the instructions for coupling are stored in a server.

In an embodiment, the patient interface is adapted for transmission over a network to a remote location.

In an embodiment, the content interface is adapted for transmission over a network to a remote location.

In an embodiment, the patient interface includes a series of questions.

In an embodiment, a system for recruiting a patient into a clinical trial further comprises instructions for coupling at least a portion of the patient-specific data to the clinical trial.

In an embodiment, a system for recruiting a patient into a clinical trial further comprises instructions for coupling a set of trial contact information to the patient.

In an embodiment, the patient-specific data comprises at least one of patient contact information, disease of concern, demographic data, drug classes of interest, prior therapies, specific drugs of interest, years since diagnosis, stage of disease, phase of clinical trial, and concomitant diseases.

In an embodiment, a system for recruiting a patient into a clinical trial comprises a patient database, residing on a server and including a set of patient-specific data; a criteria interface coupled to the server over a network; a set of clinical trial criteria corresponding to the clinical trial and collected through the criteria interface; and instructions for comparing the set of clinical trial criteria to the set of patient-specific data to determine whether a match exists between the patient and the clinical trial.

In an embodiment, a method for recruiting a patient into a clinical trial comprises serving a content interface by a server to a first remote location over a network; receiving a set of disease-specific data from the content interface over the network, the set of disease-specific data collected from a disease expert through the content interface; serving a patient interface by the server to a second remote location over the network; receiving a set of patient-specific data from the patient interface over the network, the set of patient-specific data collected from the patient through the patient interface; filtering the set of patient-specific data in comparison to the set of disease-specific data to generate a set of patient-disease characteristics; comparing the set of patient-disease characteristics to a set of trial-specific criteria corresponding to the clinical trial; and determining whether a match exists between the patient and the clinical trial.

In an embodiment, a method for recruiting a patient into a clinical trial comprises compiling a patient database including a set of patient-specific data; storing the database on a server; serving a criteria interface from the server to a remote location over a network; receiving a set of clinical trial criteria corresponding to the clinical trial from the criteria interface; and comparing the set of clinical trial criteria to the set of patient-specific data to determine whether a match exists between the patient and the clinical trial.

In an embodiment, a computer program product, disposed on a computer readable medium for recruiting a patient into a clinical trial, comprises instructions for causing a processor to serve a content interface to a first remote location over a network; receive a set of disease-specific data from the content interface over the network, the set of disease-specific data collected from a disease expert through the content interface; serve a patient interface by the server to a second remote location over the network; receive a set of patient-specific data from the patient interface over the network, the set of patient-specific data collected from the patient through the patient interface; filter the set of patient-specific data in comparison to the set of disease-specific data to generate a set of patient-disease characteristics; compare the set of patient-disease characteristics to a set of trial-specific criteria corresponding to the clinical trial; and determine whether a match exists between the patient and the clinical trial.

In an embodiment, a method of recruiting a patient into a clinical trial comprises receiving patient-specific data from a remote network device at a server; accessing criteria of more than one clinical trial at the server; and determining one or more clinical trials having criteria satisfied by the patient-specific data.

In an embodiment, a server system for recruiting a patient into a clinical trial comprises sets of criteria corresponding to a different clinical trial; instructions for receiving patient specific data from a remote network device; and instructions for determining one or more clinical trials having criteria satisfied by the patient specific data.

BRIEF DESCRIPTION OF THE FIGURES

FIG. 3 depicts exemplary disease information.

FIGS. 4-6 depict exemplary questions to be answered by a patient.

FIG. 11 depicts an exemplary registration form for a user of the system to complete.

FIG. 16 depicts an exemplary disease interface.

FIG. 18 depicts an exemplary type selector.

FIG. 19 depicts an exemplary option count selector.

FIG. 20 depicts an exemplary question editor.

FIGS. 21-22 depict an exemplary trial association interface.

FIG. 23 depicts an exemplary criterion interface.

FIG. 25 depicts an exemplary test interface.

FIG. 25A depicts exemplary test results.

FIGS. 26-27 depict exemplary questions to be answered by a patient.

FIG. 28 depicts exemplary match results.

DETAILED DESCRIPTION

Figure 1:
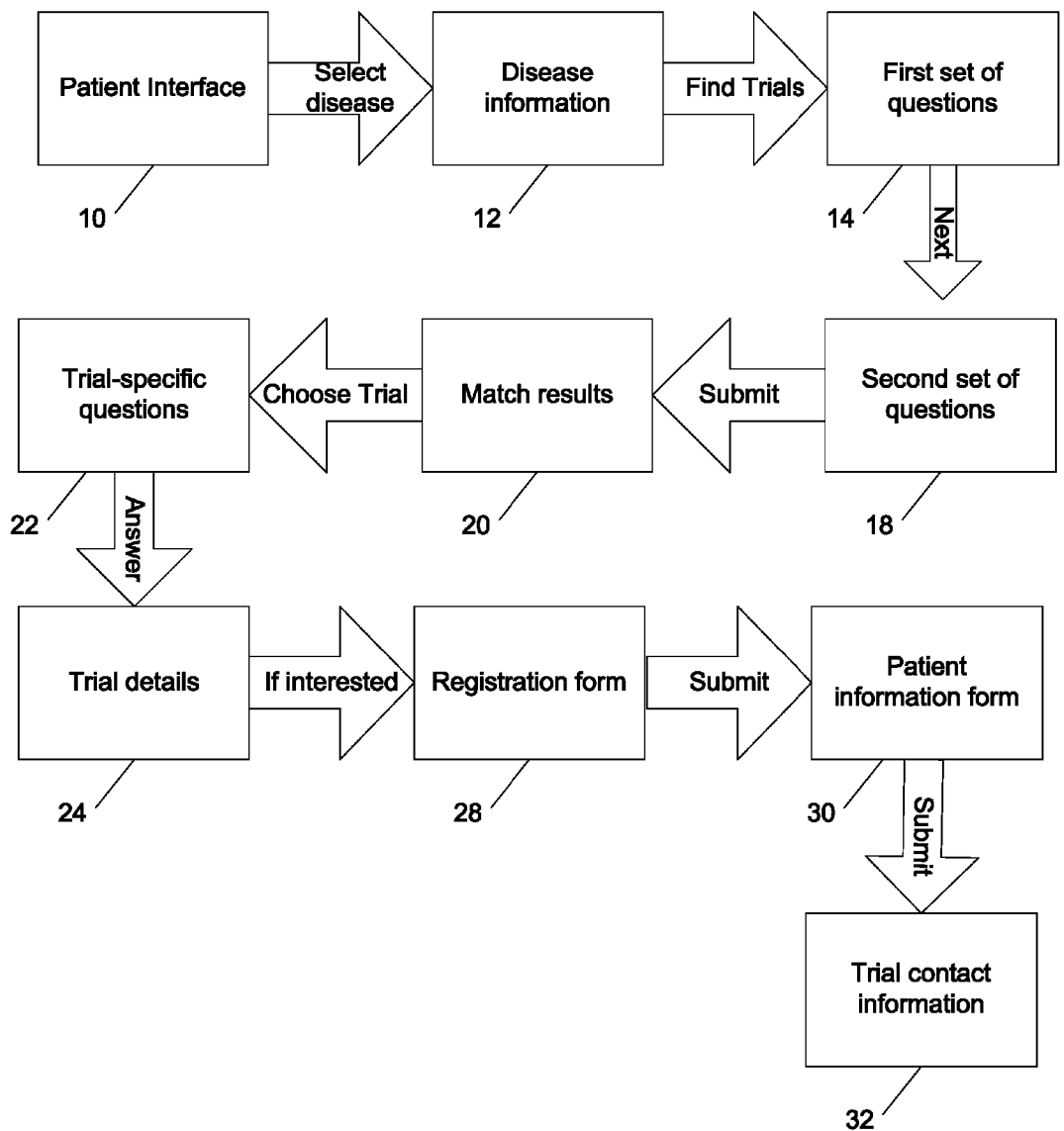
FIG. 1 depicts a flowchart of a process for a patient attempting to match to a clinical trial.

Described herein are techniques that can facilitate the matching of public and clinician interest in novel therapies with a comprehensive, secure database of public and private clinical trials to promote patient recruitment.

In an embodiment, the present disclosure describes techniques that can facilitate clinical trial recruitment using a network. In particular, the disclosure describes an approach for accelerating clinical trial recruitment by matching patient data submitted over the Internet to server-side maintained databases of public and private clinical trials in a secure manner so that patient information and proprietary clinical trial information are not compromised.

The system and method are implemented in part by a matching procedure, a security application and protocol, and patient and public and private clinical trial databases. The present disclosure also contemplates experimental treatment content review and analysis by experts to promote patient and clinician understanding.

In an embodiment, the patient, or clinician on behalf of the patient, inputs information including disease of concern, basic demographic data, drug classes of interest, prior therapies, specific drugs of interest, years since diagnosis, stage of disease, phase of clinical trial, other known diseases or infections, and various physiological, biochemical, and pathological parameters applicable to the disease of concern into the patient interface. The patient is presented different "levels" of questions and can answer as many as he/she feels comfortable. Once the patient-specific data is submitted, the server requests a match of the patient data to a clinical trials database maintained in the system. The rules-based matching algorithm compares a patient's eligibility criteria to the public and private trials in the database.

In another embodiment, the recruiting system uses security protocols to ensure that private data is kept confidential and to sanitize the information passed on to the client system. The security application layer of the network monitors all protocols that are sent back and forth to the databases and allows the components of the system to remain autonomous. The security application may send only the data necessary for trial matching, a patient's eligibility criteria, to the trials database. Private trial data is not accessible via the web, while public trial data is displayed.

In yet another embodiment, pharmaceutical companies can post trial data or trial-specific criteria in the recruitment system to facilitate trial recruitment. The system may serve as an independent third-party hub for proprietary trial data. As a third party, the systems facilitates a marketplace that is structurally impossible for pharmaceutical companies, contract research organizations (CROs) and individual health portals to build. The system offers the necessary components of a trials marketplace: comprehensiveness, lack of bias (e.g., no 'selling' of particular trials), and transparency of market operation.

In another embodiment, pharmaceutical company can access the patient database to pre-enroll patients into clinical trials. Access to the patient database will accelerate patient recruitment and enhance the probability of attaining an appropriate patient population for a specific trial. As patients register through the patient interface, a database of patients who are interested in entering clinical trials is populated, eventually allowing new trials to be more fully enrolled prior to initiation.

The recruitment system may include a secure database system that matches patients with appropriate clinical trials while keeping proprietary trial information hidden.

In one practice, to match to a clinical trial in the trial database, patients and health professionals submit information to the system using a web-based patient interface. In an embodiment, the server generates Hyper-Text Markup Language (HTML) code or code in a similar language such as XML or GML to display the patient interface on a web page and to receive the patient-specific data submitted from a web page. Patients may enter information including contact information, disease of concern, basic demographic data, drug classes of interest, prior therapies, specific drugs of interest, years since diagnosis, stage of disease, phase of clinical trial, other known diseases or infections, and various physiological, biochemical, and pathological parameters applicable to the disease of concern. The patient may answer as many questions on the clinical trials questionnaire as he/she feels comfortable but answering more questions may result in better targeted trial matches.

Once a patient submits at least a portion of the patient-specific data, the server requests a match of the patient data to public and private clinical trials in the database. In one embodiment, the matching algorithm used by the system is rules-based. Upon entry of a new clinical trial into the system, the trial site coordinator or pharmaceutical company can determine the desired accuracy of patient matches. The rules-based matching system allows trial site coordinators and pharmaceutical companies to control the accuracy of patient matches, giving them great flexibility in matching to a desired patient pool. The rules-based system allows some trial sites to accept only patients that match 100% of the trial-specific criteria, while other trial sites can remain more lenient and require a lower matching percentage. A "match" exists for a trial if the patient-specific data submitted successfully passes enough of a trial's eligibility criteria to meet the specified percentage.

In an embodiment, the patient-specific data questions are organized by levels and presented to the patients through the patient interface on a level-by-level basis to maintain a user-friendly environment. The first level of questions may serve as an initial screening where patients are asked to submit basic information about their age, gender, and disease of concern. As a patient proceeds with the process and progresses to other levels in the patient interface, the questions become more detail-orientated and disease-specific.

In an embodiment, the match data may pass through a multi-tiered security layer and protocol to sanitize the information passed on to the client system. For non-proprietary trials, details such as contact information (i.e., name, phone number, and email address), trial description, trial location, drugs being tested, and eligibility criteria are displayed. For proprietary trials, unless otherwise specified, only trial contact information is displayed. All confidential proprietary trial details are hidden. Once the clinical trial data is sanitized by the security layer and protocol, the match results are sent to the server. The server formats the results for reporting to the patient. In an embodiment, the server generates HTML code to display the results on a web page.

In an embodiment, the proprietary trial and patient information is protected from unauthorized access. The secure database system protects sensitive pharmaceutical information (e.g., trial site locations, drugs in development, and trial eligibility criteria) while allowing trials to be matched to appropriate patients. The database system includes safeguards from hacking and spoofing while allowing pharmaceutical companies to alter the level of information disclosure based upon accrual need. This is accomplished by using security protocols utilizing fine grain access control, highly redundant firewall/security systems, off-line storage of the most sensitive information as well as traditional safeguards such as 128-bit Secure Socket Layer ("SSL") encryption, unique identifiers, maximum number of requests per user per hour, and so forth. Patient information is also protected in this controlled environment, and will only be released to specifically designated partners with the patients' active consent.

In an embodiment, security measures that may be taken to ensure secure access to the databases include multi-tiered architecture; multiple firewalls; security reinforcement at the database level; off-line loading process for private trial data; fine-grained access control; and SSL encryption.

To match to a clinical trial in the trial database, a disease expert submits a set of disease-specific data via the content interface. A set of questions based upon the disease-specific data is presented to patients and health professionals via the patient interface. The patients and health professionals provide patient-specific data to the system in the form of responses to the questions. The patient-specific data is compared to the disease-specific data to determine a set of patient-disease characteristics. These characteristics are then compared to clinical trial eligibility criteria, and the existence of a match determined.

In an embodiment, the questions presented via the patient interface are organized by levels and presented to the patients on a level-by-level basis. The level-based approach to the questionnaire enables patients to filter trials gradually without being overwhelmed by an extensive list of trial-specific questions.

In an embodiment, patients have access to experimental treatment content created by experts. This content is made available through the patient interface. In an embodiment, the experts include Harvard M.D. editors. The content is provided to assist patients with answering accurately as many questions as possible in order to receive well-targeted trial results.

The content and clinical trials made available through the patient interface may focus on the following and other diseases: AIDS/HIV; Allergic Disorders; Alzheimer's Disease; Anxiety Disorders; Asthma; Bipolar Disorder; Bladder Disorders; Brain Tumors; Breast Cancer; Chronic Obstructive Pulmonary Disease; Chronic Pain; Colon Cancer; Congestive Heart Failure; Coronary Heart Disease; Crohn's Disease; Cystic Fibrosis; Depression; Diabetes; Ear, Nose, & Throat Disorders; End Stage Renal Disease; Endometriosis; Epilepsy; Fertility Treatments; Foot Disorders; Gastrointestinal Disorders; Glaucoma; Hepatitis C; High Blood Pressure;

High Cholesterol; HIV; Hodgkin's Disease; Hypertension; Incontinence; Infertility; Inflammatory Bowel Disease; Leukemia; Acute Lymphoid Leukemia; Acute Myeloid Leukemia; Chronic Lymphoid Leukemia; Chronic Myeloid Leukemia; Lung Cancer; Lupus; Lymphoma; Non-Hodgkin's Hodgkin's Lymphoma; Menopause; Migraines; Multiple Sclerosis; Neuropathy; Obesity; Oral Disorders; Osteoarthritis; Osteoporosis; Ovarian Cancer; Pancreatic Cancer; Parkinson's Disease; Prostate Cancer; Psoriasis; Recurrent Pregnancy Loss; Reproductive Conditions; Rheumatoid Arthritis; Schizophrenia; Sexual Dysfunction; Sickle Cell Anemia; Skin Cancer; Skin Disorders; Sleep Disorders; Spinal Cord Injury; Stroke; Ulcerative Colitis; Uterine Fibroids; and Vascular Disorders.

A number of non-limiting examples will now be presented to illustrate more fully several aspects of the foregoing subject matter.

FIG. 1 depicts a flowchart of an embodiment in which a patient seeks to find matches to clinical trials for lung cancer therapies. In an embodiment, the patient connects to the patient interface 10 and requests disease information 12 specific for a certain disease or disease class. In an embodiment, a server (not shown) serves the interface 10 in the form of an HTML-encoded web page to a remote client (not shown). The patient may then elect to search for matching trials. The server then serves an initial set of questions 14 to collect, e.g., demographic data about the patient and the disease of interest to the patient.

After answers are submitted by the patient interface 10 to the server, the server serves a second set of questions 18 which address more specific detail than did the initial set of questions 14. Questions included among the second set 18 may request information including drug classes of interest, prior therapies, specific drugs of interest, years since diagnosis, stage of disease, phase of clinical trial, other known diseases or infections, and various physiological, biochemical, and pathological parameters applicable to the disease of concern, in addition to other information. The answers to these questions are submitted by the interface 10 to the server.

The server then compares the responses to the first set of questions 14 and the second set of questions 18 to a set of criteria for a given clinical trial. If a match exists, then the trial is included in a set of match results 20. If a patient is interested in pursuing a particular trial listed among the match results 20, the server will then serve a set of trial-specific questions 22, if any exist for the trial. The answers to the trial-specific questions 22 will be compared to the trial-specific specific criteria to determine whether a match still exists. If it does, then the server will serve a set of trial details 24. If the patient wishes to learn how to enroll in the trial, the patient completes a registration form 28 and a patient data form 30. The server then serves trial contact information 32 to the patient.

In an embodiment, the server may perform a comparison of the patient answers to the set of criteria for a given clinical trial at any time. For example, a comparison may be performed between the responses to only the first set of questions 14 and the trial criteria.

Figure 2:
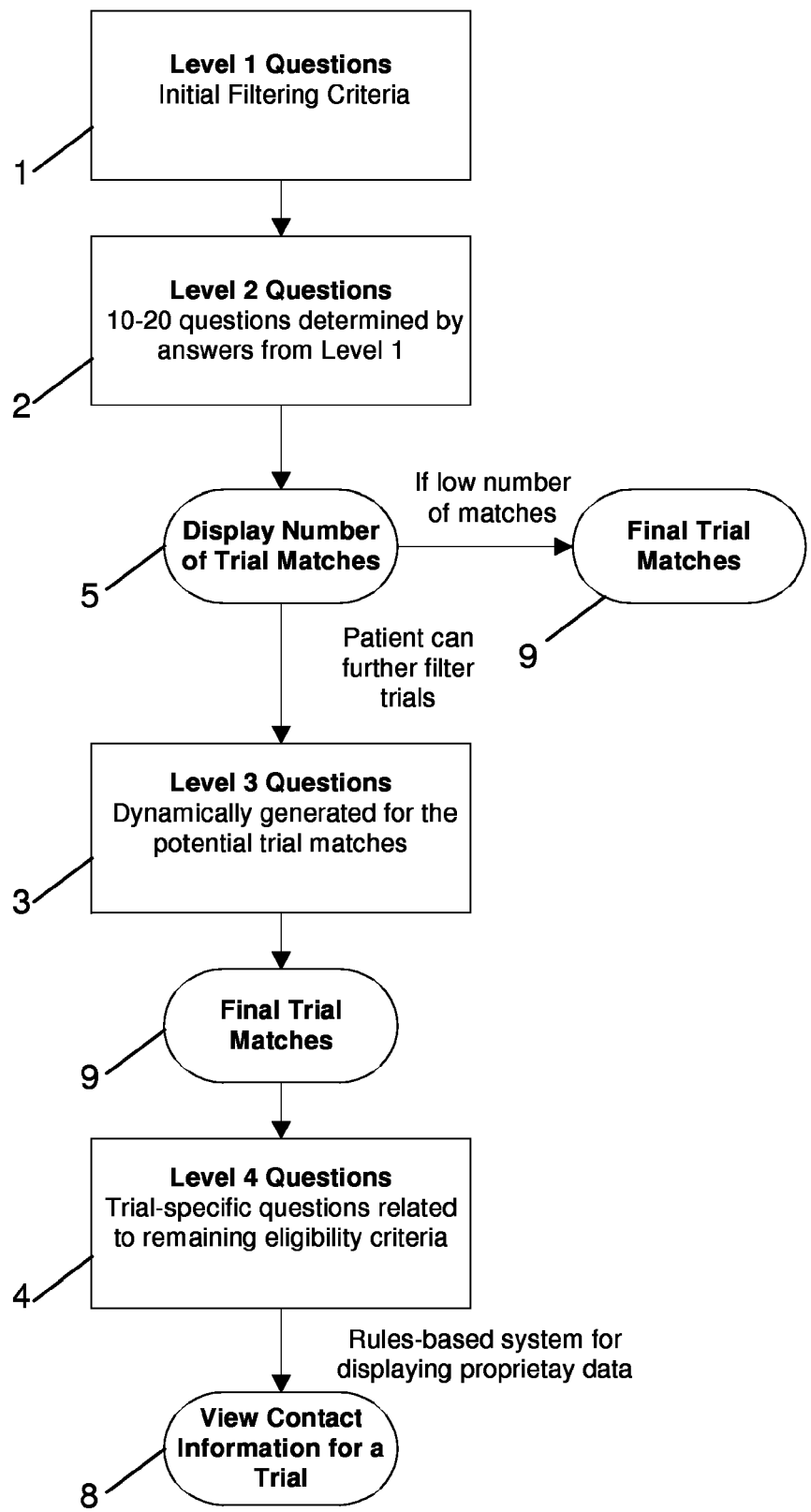
FIG. 2 depicts a flowchart of a process for recruiting a patient into a clinical trial.

FIG. 2 depicts another embodiment, in which a first level of questions 1 in the patient interface serves as an initial screening where patients are asked to submit basic information, e.g., about their age, gender, and disease of concern. As a patient proceeds with the process and progresses to other levels, the questions become more detail-orientated and disease-specific.

The questions presented in a second level 2 of the questionnaire are determined by the patient's response in level one. The number of trial matches 5 may be displayed. At any point, if a patient matches a small number of trials, the patient has the option to view the match results 9. As the patient progresses with the process, the level 3 questions 3 are dynamically generated and, thus, are specific to the remaining potential trial matches. Finally, in level 4, the patient is presented with any unanswered questions 4 applicable to a selected trial's eligibility criteria, ensuring that the patient fully meets a trial's eligibility. Once match results 9 have been displayed, trial contact information 8 may be viewed.

In an embodiment, one or more levels of questions may be omitted. For example, the system may be configured so that all data necessary to test for the existence of a match is collected from the first level of questions. In another embodiment, the set of patient-specific data generated from answers to level one questions may be sufficient to meet or exceed the specified matching percentage for a given trial; in such a circumstance, the remainder of the questionnaire may be discarded and the match results reported immediately to the patient.

Figure 3:
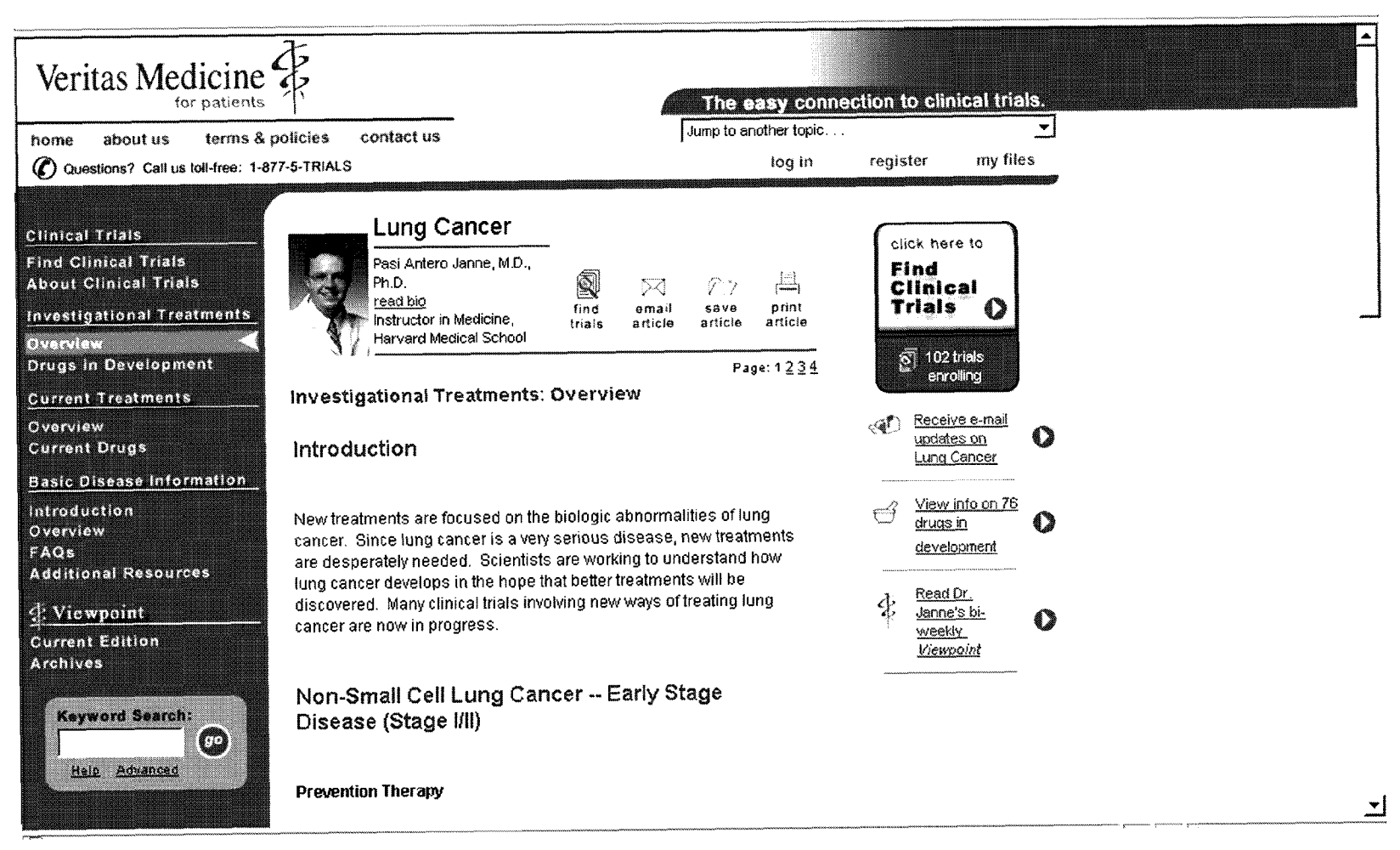

FIG. 3 depicts one embodiment of disease information 12 when the patient interface 10 comprises a set of web pages. Disease information 12 may include information about a disease of interest 302, an expert 304 providing the content, background material 308, therapy information 310, such as information on, e.g., prevention therapy, combination therapy, pre-surgical and post-surgical therapy, chemotherapy before, during, and after radiation therapy, and other therapeutic modalities known to one of ordinary skill in the art. Disease information 12 may also provide means for initiating a trial search 312.

FIG. 4 depicts one embodiment of the first set of questions 14. Questions may include, e.g., date of birth 402, geographic location and preferences 404, diagnosis 408, and type and stage (not shown).

Figure 5:
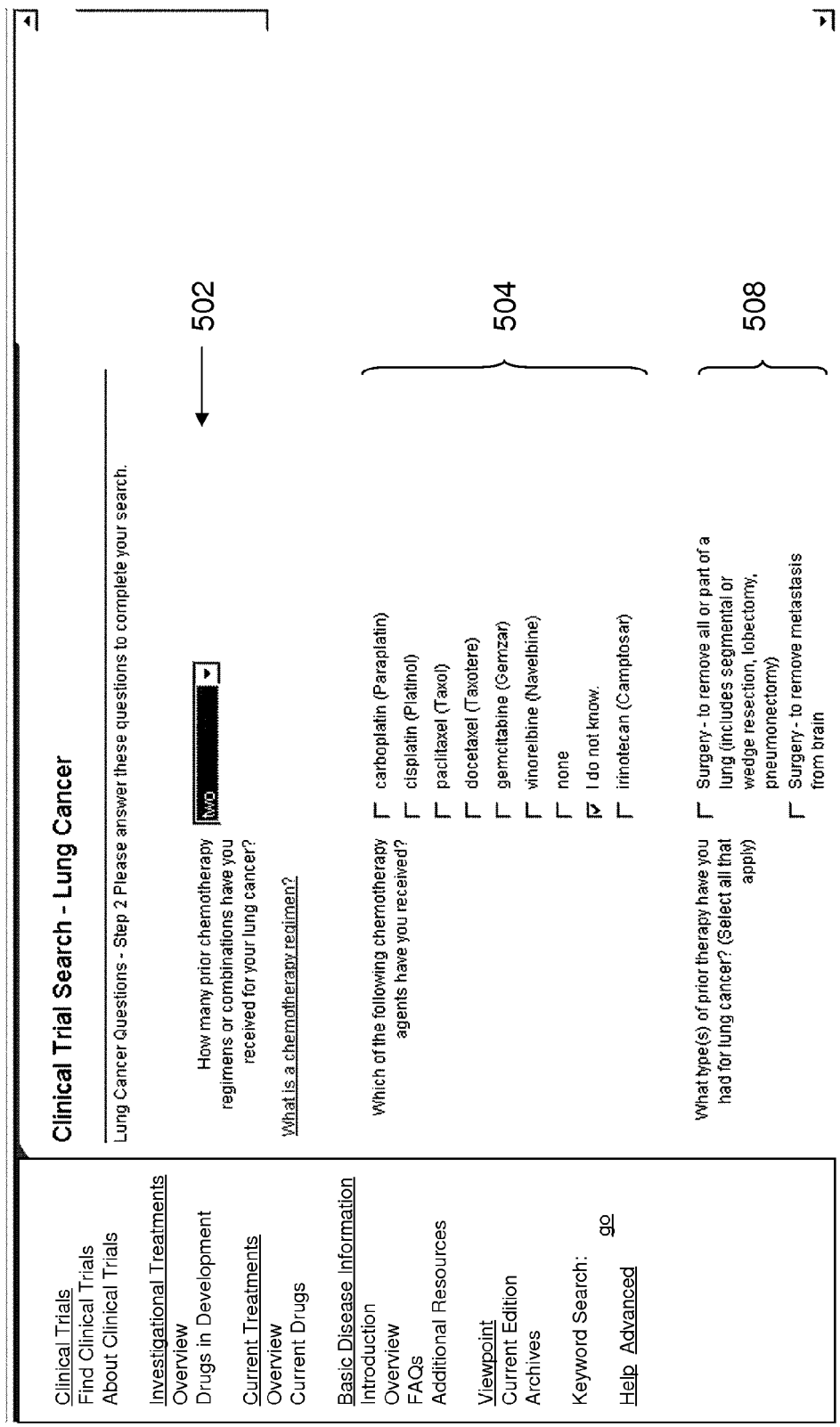
Figure 6:
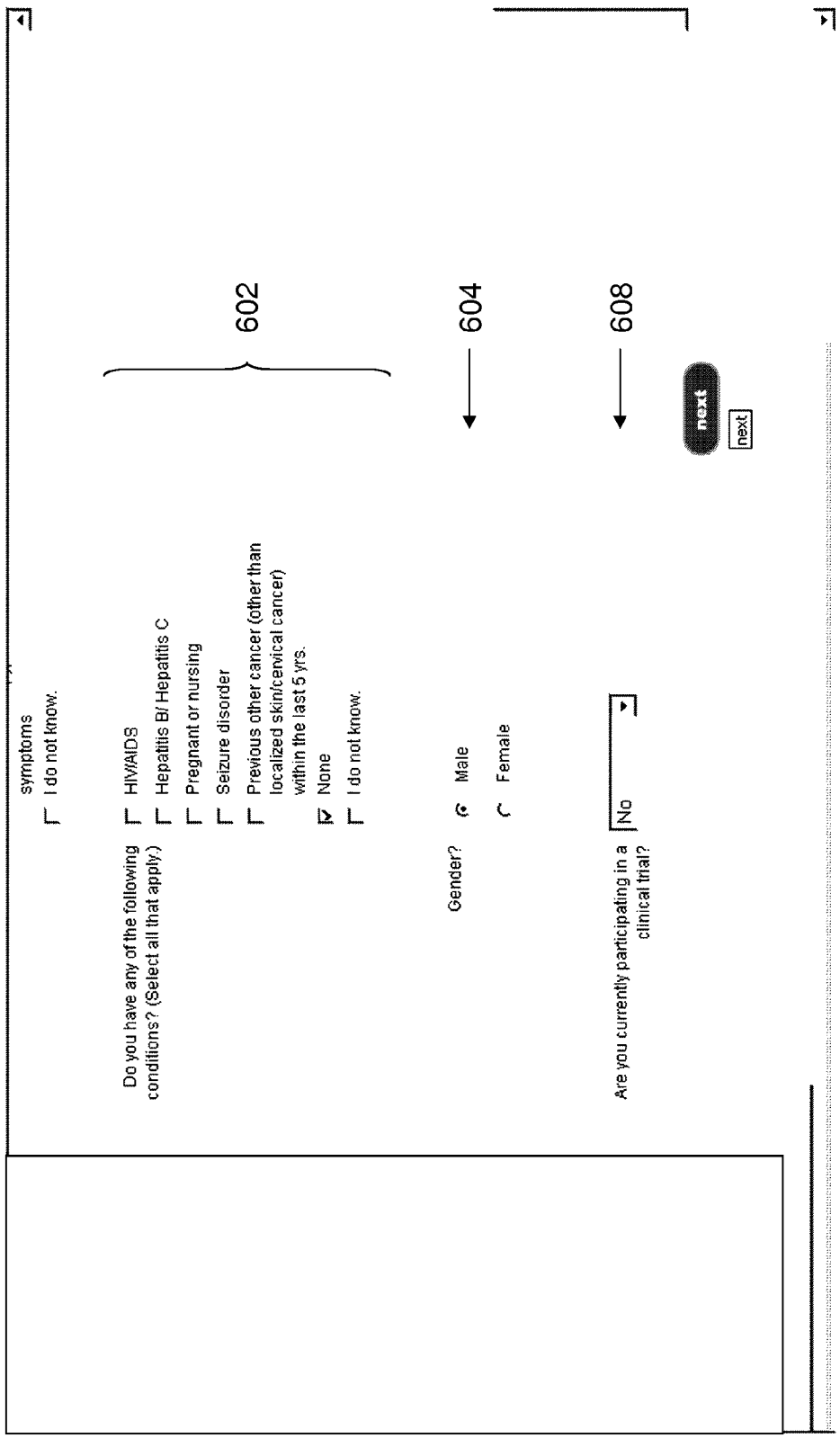

FIGS. 5 and 6 depict one embodiment of the second set of questions 18. Questions may include, e.g., number of prior therapy regimens 502, drug therapies undergone 504, other therapy modalities undergone 508, concomitant illnesses 602, gender 604, participation in clinical trials 608, and other specific questions regarding, e.g., duration of diagnosis, organ involvement, family history, exacerbating conditions, and any other questions that expert 304 deems relevant.

Figure 7:
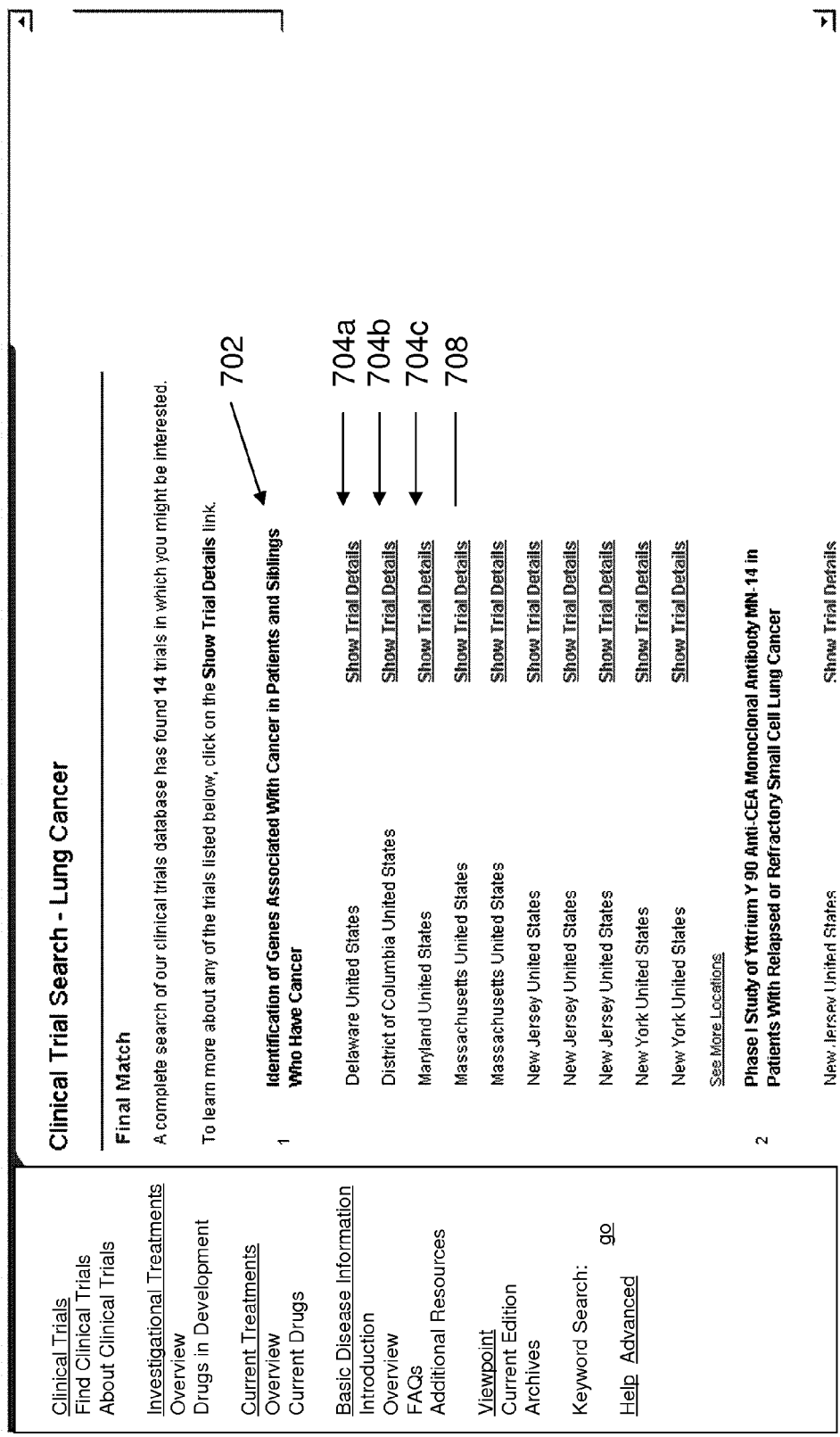
FIG. 7 depicts exemplary trial match results.

FIG. 7 depicts an embodiment of match results 20. A trial match 702 may include a series of trial sites 704a, 704b, and 704c. The match results 20 may provide means for selecting a trial 708.

Figure 8:
FIG. 8 depicts an exemplary trial-specific question to be answered by a patient.

FIG. 8 depicts an embodiment of a set of trial-specific questions 22. A trial specific question 802 may be a very specific question, the answer to which alone may determine whether a patient matches to a trial.

Figure 9:
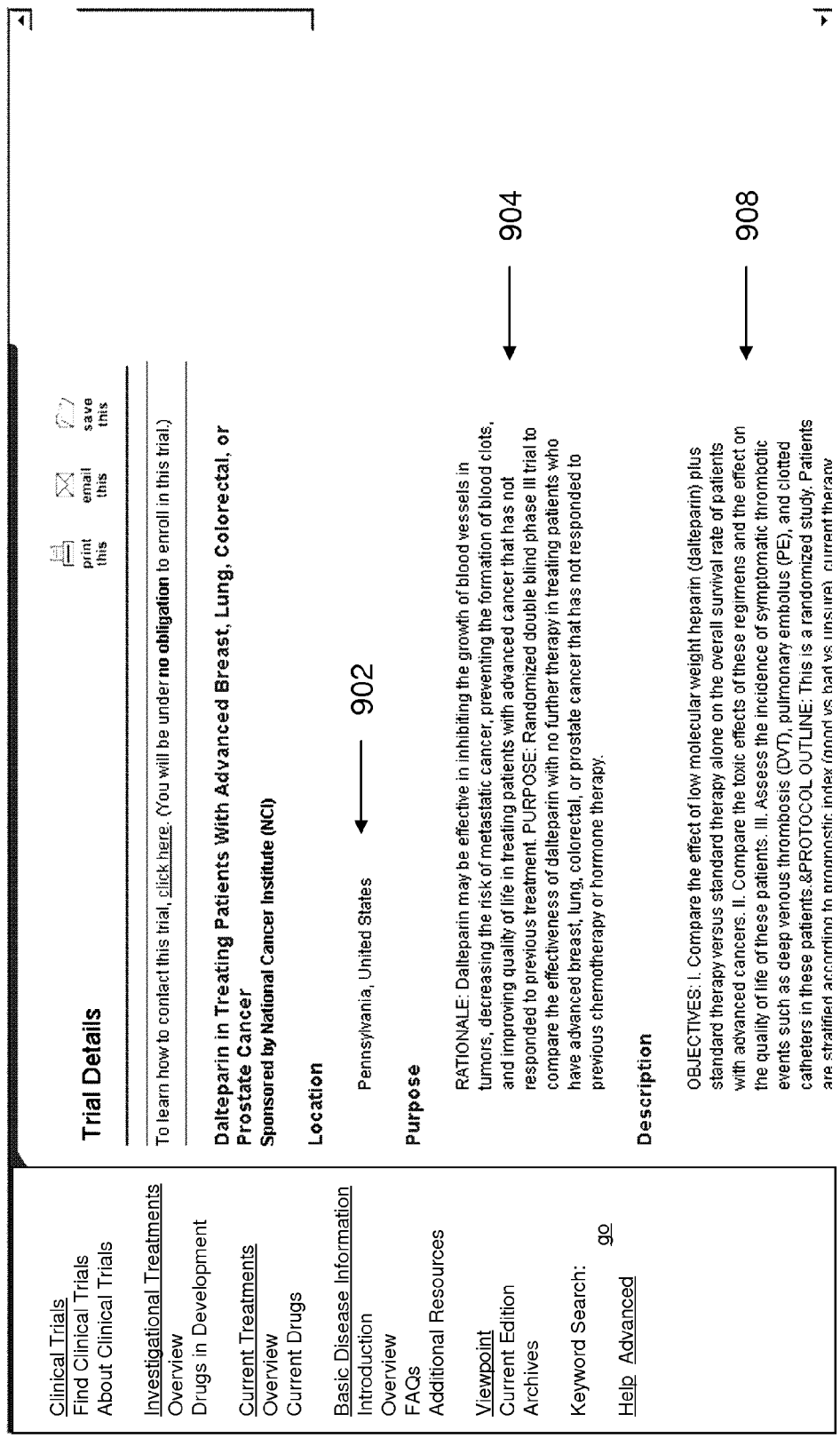
FIGS. 9-10 depict exemplary trial details.
Figure 10:
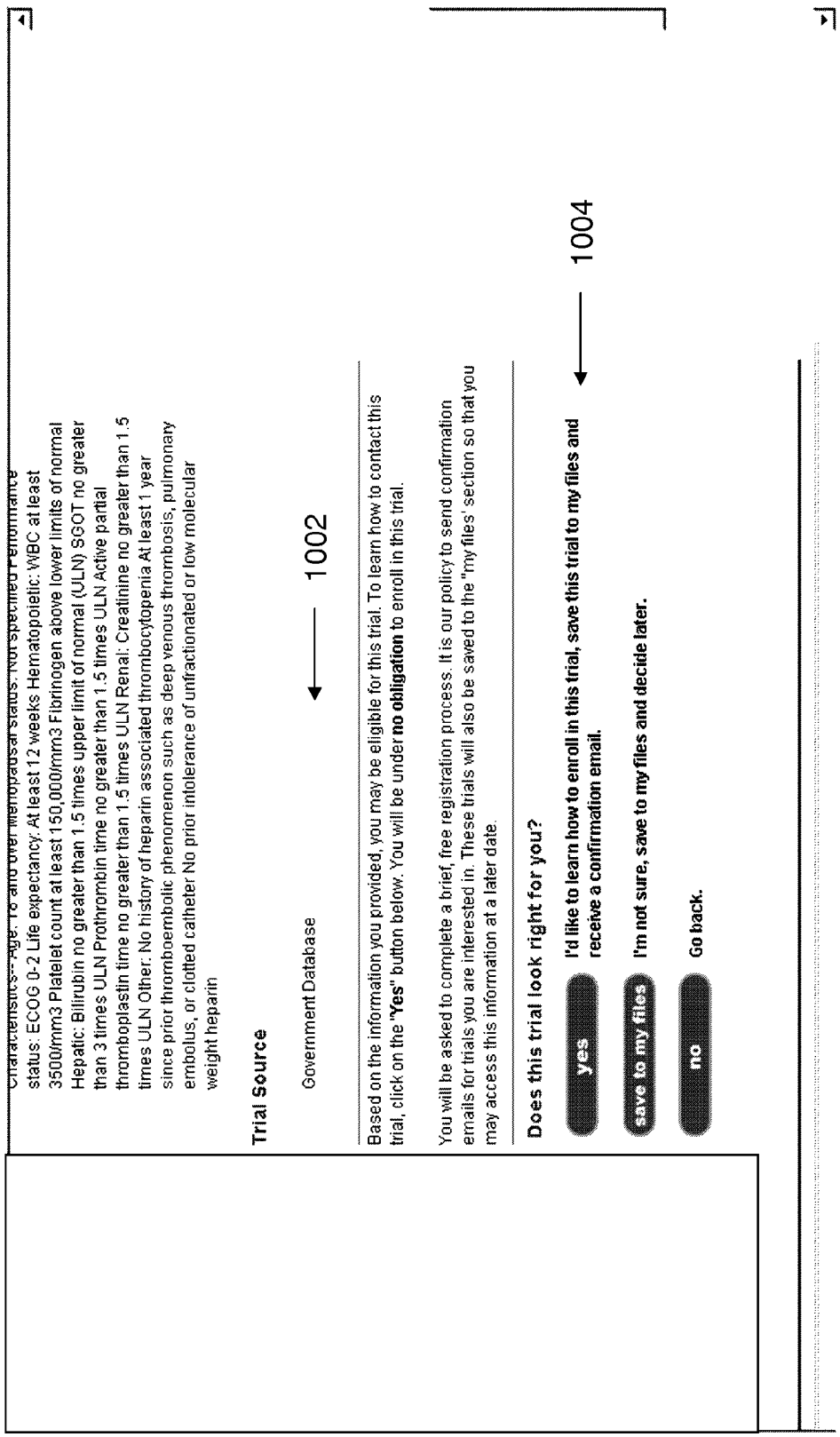

FIGS. 9 and 10 depict an embodiment of a set of trial details 24. The trial details 24 may include information concerning the location 902, the purpose 904, a detailed description 908, eligibility criteria, trial source 1002, data on drugs used in the trial, and other details known to be relevant by one of ordinary skill in the art. The trial details 24 may include means for requesting enrollment information 1004.

FIG. 11 depicts an embodiment of registration form 28, which may request, e.g., login data 1102, contact data 1104, and verification data 1108.

Figure 12:
FIG. 12 depicts an exemplary patient data form for a user of the system to complete.

FIG. 12 depicts an embodiment of patient data form 30, which may request, e.g., non-unique identifying data 1202.

Figure 13:
FIG. 13 depicts exemplary trial contact information.

FIG. 13 depicts an embodiment of trial contact information 32, which may include trial title 1302, trial sponsor 1304, trial location 1308, and trial contact entity 1310.

Figure 14:
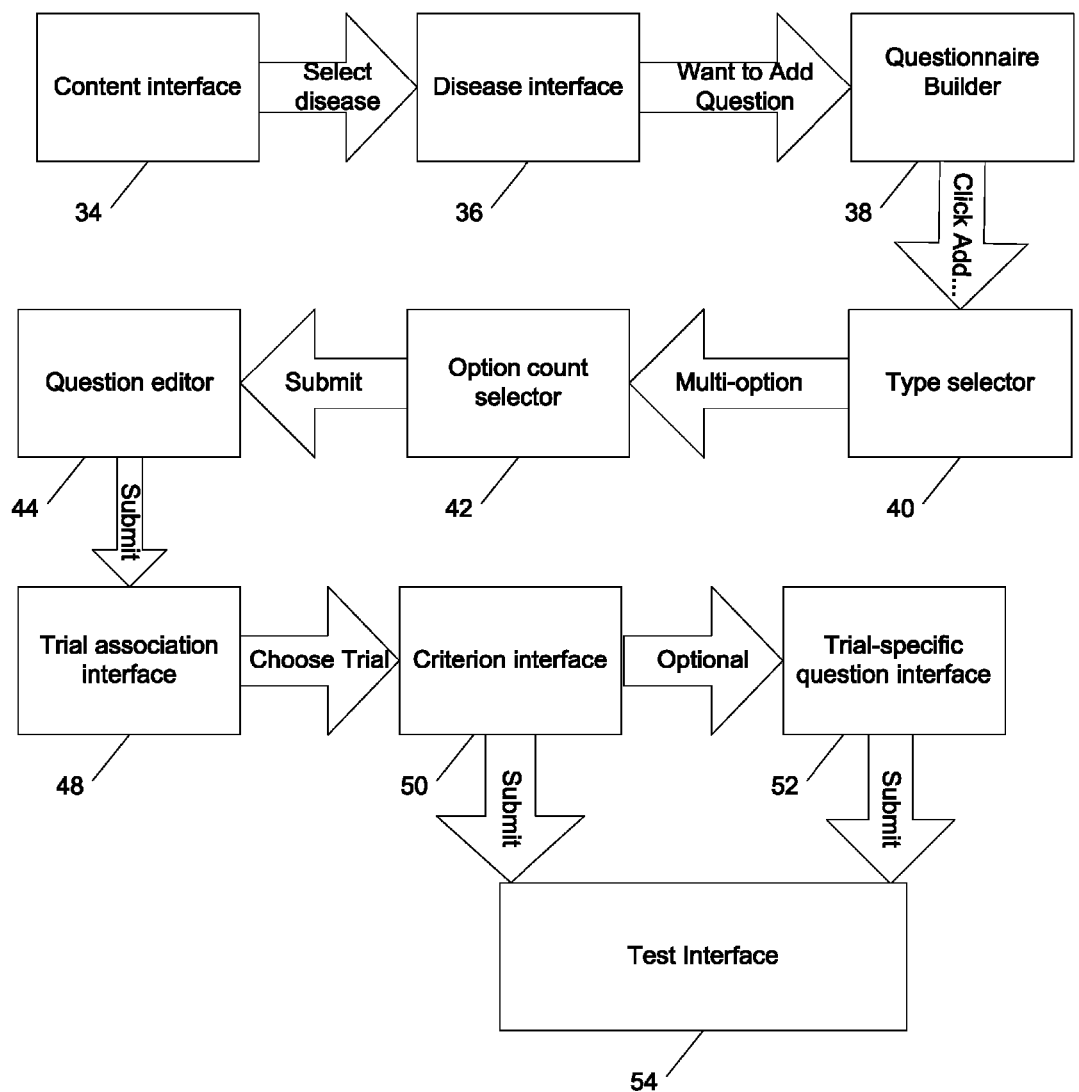
FIG. 14 depicts a flowchart of an expert providing content for a recruiting system.

FIG. 14 depicts a flowchart of an embodiment in which an expert provides content for questions through a content interface 34. The server serves the content interface 34 to an expert, such as expert 304. The expert selects a disease for which content is to be provided, and the server serves a disease interface 36. From disease interface 36, expert 304 may modify disease information 12 and may add or modify questions for first set 14, second set 18, and for trial-specific questions 22.

If expert 304 elects to add a new question, server serves a questionnaire builder 38. Builder 38 includes a question type selector 40, option count selector 42, and question editor 44. Once expert 304 has created a new question, the question is then associated with a trial through the trial association interface 48. The server then serves a criterion interface 50 to permit expert 304 to specify whether a question constitutes an inclusion or exclusion criterion for the trial and what the answer should be to meet that criterion. Expert 304 may optionally add a trial-specific question using a trial-specific question interface 52. Expert 304 may verify that the question is correctly associated with the trial through a test interface 54.

Figure 15:
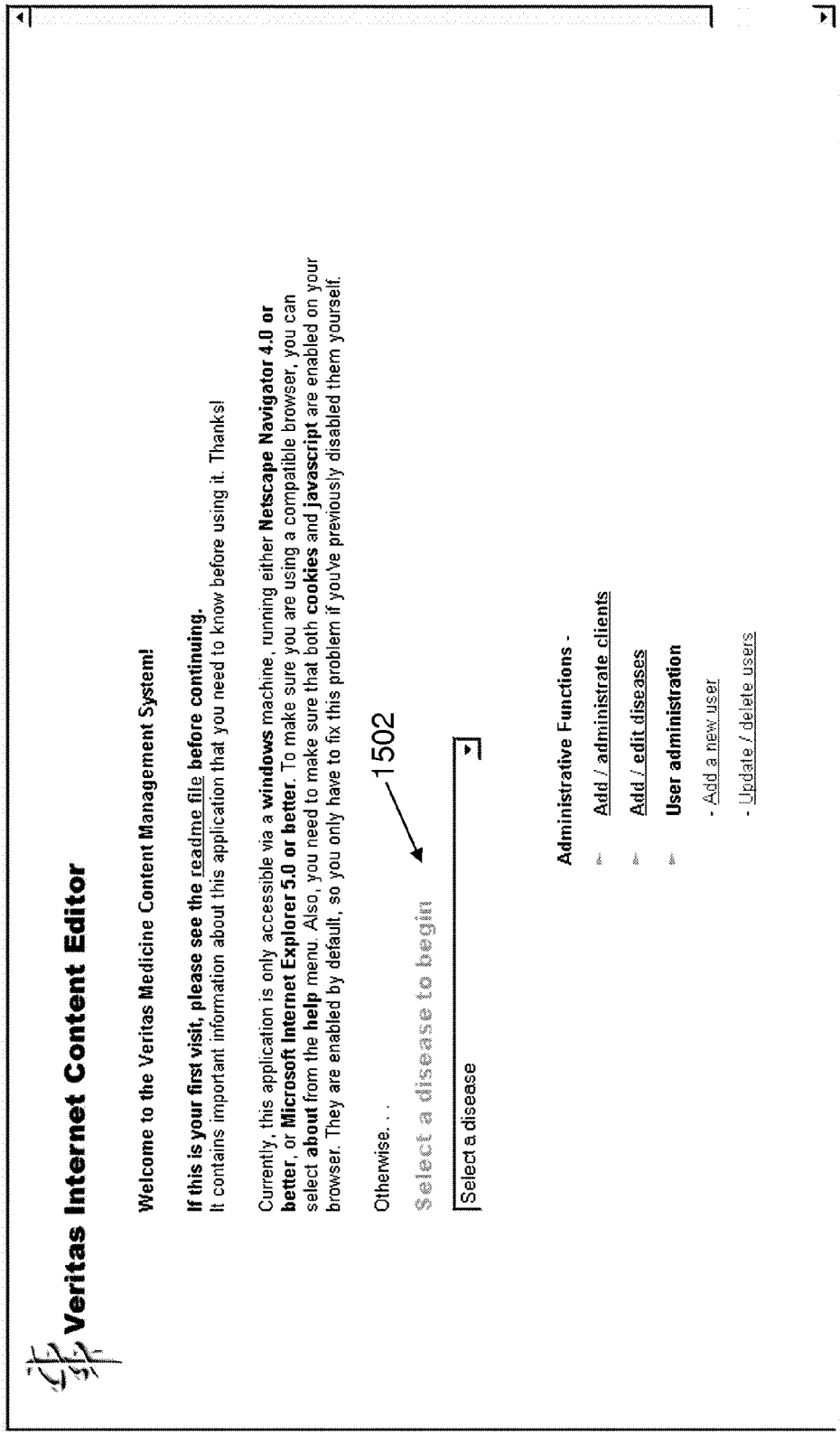
FIG. 15 depicts an exemplary content interface.

FIG. 15 depicts one embodiment of content interface 34. It may include an option to select a disease of interest 1502.

FIG. 16 depicts one embodiment of disease interface 36. It may include a disease information editor link 1602, a questionnaire builder link 1604, and a test interface link 1608.

Figure 17:
FIG. 17 depicts an exemplary questionnaire builder.

FIG. 17 depicts one embodiment of questionnaire builder 38. Builder 38 may include an add question link 1702, a reorder questions link 1704, and an edit question link 1708.

Figure 18:
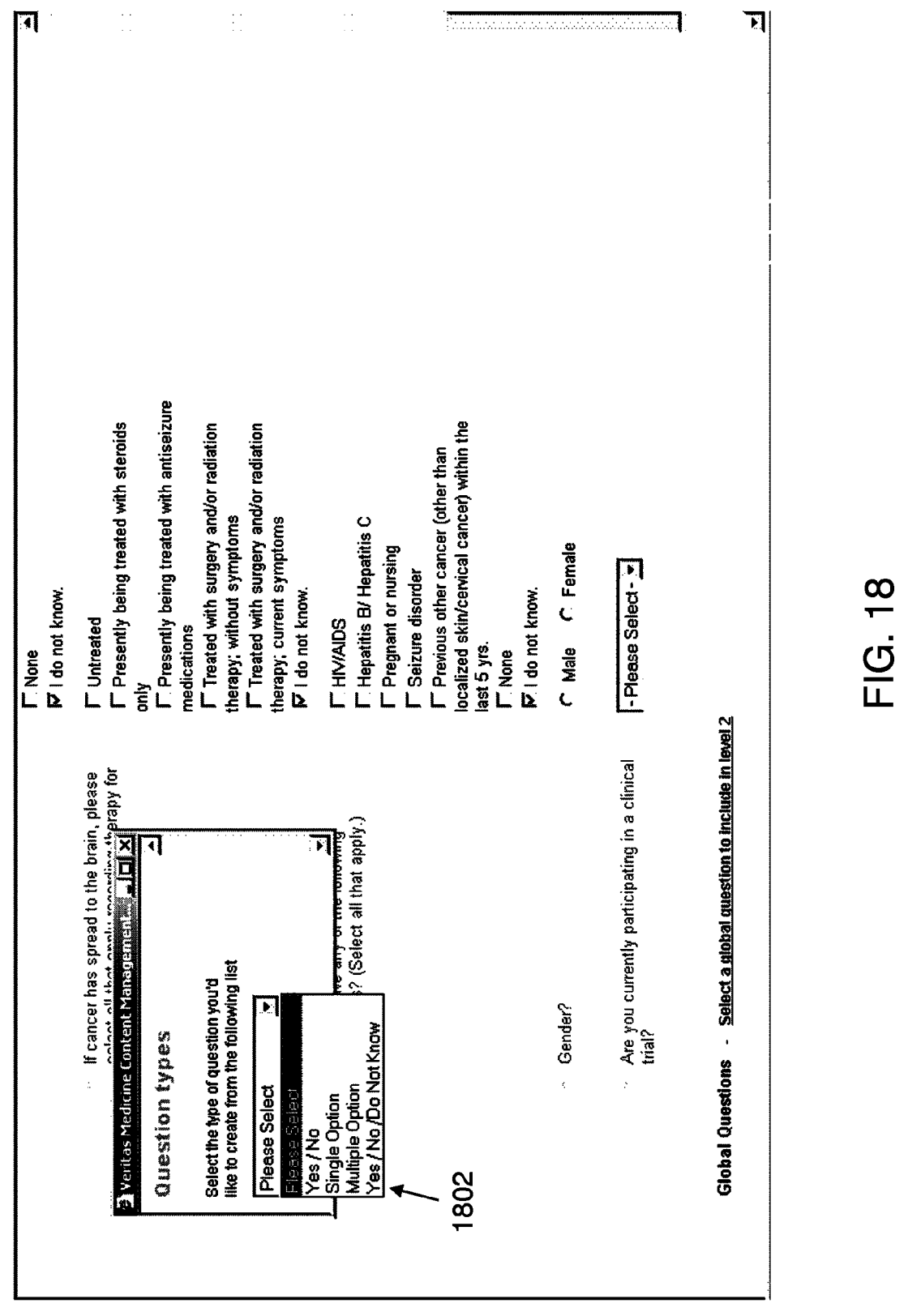

FIG. 18 depicts one embodiment of type selector 40. It may include a list of question types 1802.

Figure 19:
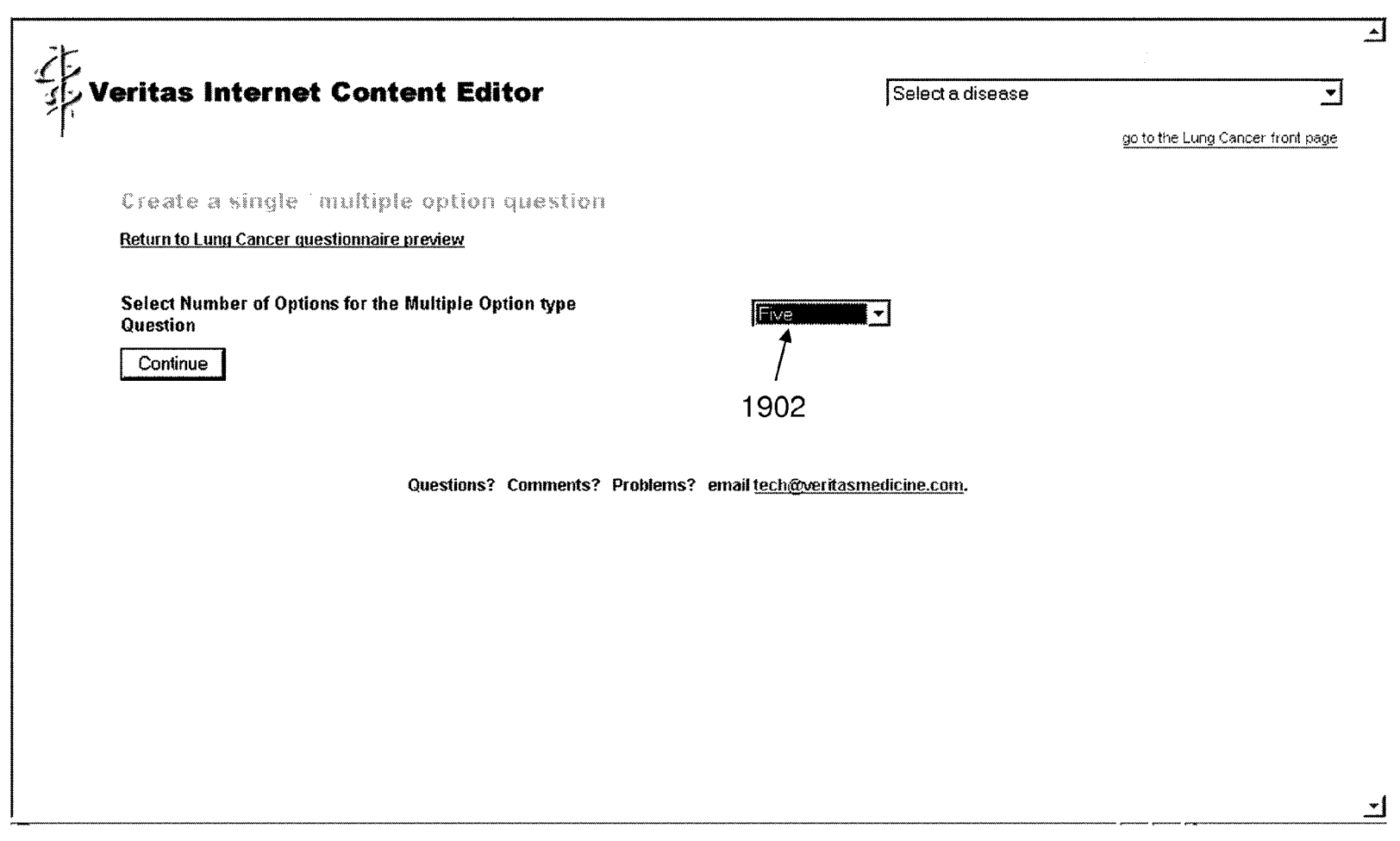

FIG. 19 depicts one embodiment of option count selector 42. Selector 42 may include a list of option counts 1902.

FIG. 20 depicts one embodiment of question editor 44. It may include a prompt 2002 to provide question text and prompts 2004 to provide answer texts. The format of prompts 2004 is determined by the options specified by expert 304 through the type selector 40 and option count selector 42.

Figure 22:
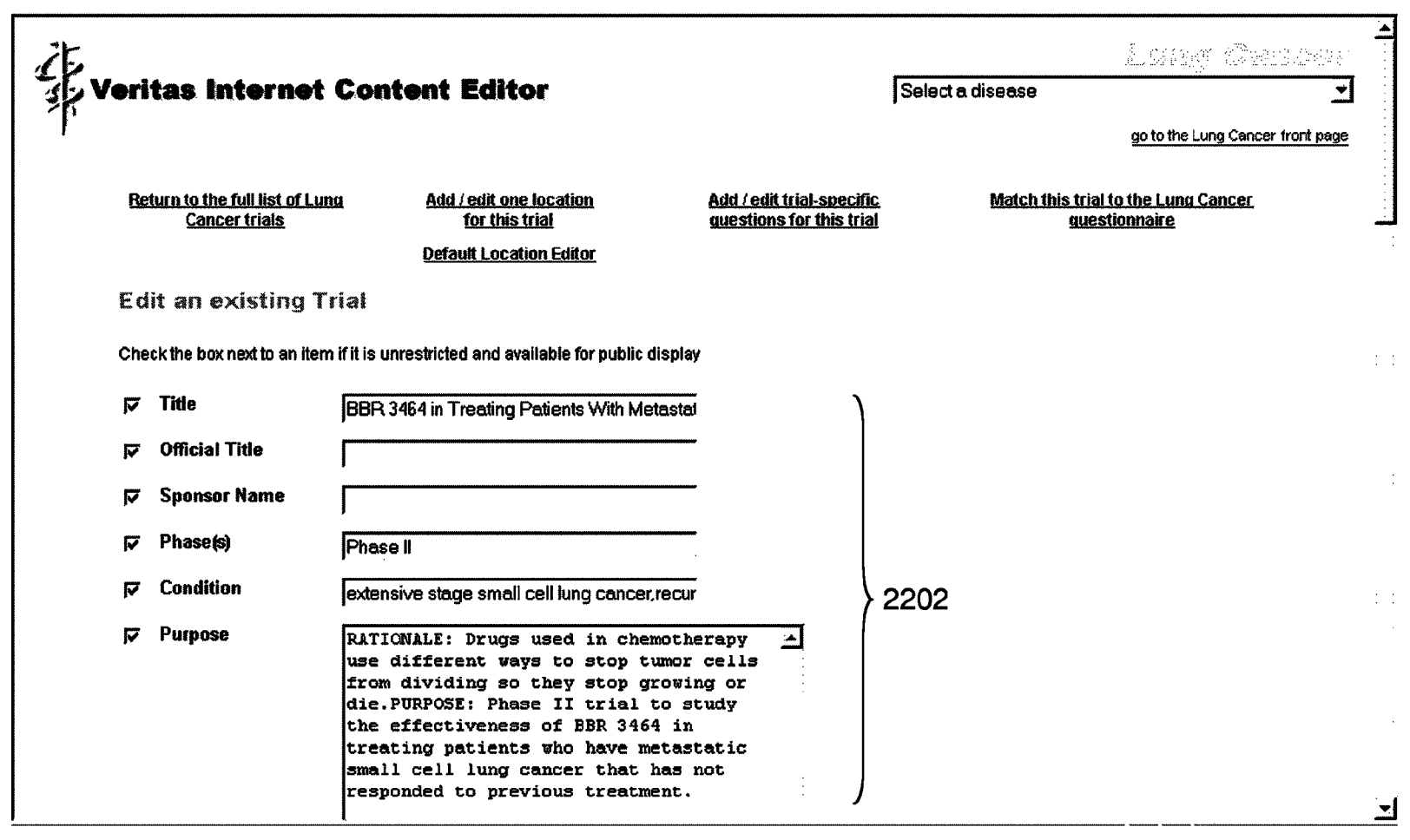

FIGS. 21 and 22 depict one embodiment of trial association interface 48, which may include a list 2102 of trials relating to the selected disease and an action selector 2104. The action selector has a list of actions including, e.g., to edit trial data, add a trial-specific question to the trial, and to associate the new question with the trial. A set of fields 2202 may be provided by which trial data may be edited.

FIG. 23 depicts one embodiment of criterion interface 50. The criterion interface 50 includes the title 2302 of the selected trial and the first set 14 and second set 18 of questions. Each question 2308 has an option indicator 2304 to permit the expert 304 to indicate whether the question is relevant for the selected trial. If a question is marked as relevant, then the patient's response to the question will be included in the comparison between the question answers and trial criteria. Expert 304 may indicate whether question 2308 is an inclusion criterion or exclusion criterion for the selected trial by choosing accordingly with a criterion selector 2310. Expert 304 may then indicate which of answers 2312 must be chosen by the patient in order to fulfill the criterion.

Figure 24:
FIG. 24 depicts an exemplary trial-specific question interface.

FIG. 24 depicts trial-specific question interface 52, which may include a question type selector 40, option count selector 42, and question editor 44, as for question builder 38. It may include a prompt 2402 for entering question text and a default selector 2404 for, e.g. a yes-or-no type question.

FIG. 25 depicts test interface 54, which includes a mock-up version 2502 of a question for expert 304 to answer.

FIG. 25A depicts the results of comparing the test responses against the trial-specific criteria. For each trial identified by trial title 2504, a set of answer matches 2508 is provided and a match percentage 2510 reported.

Figure 26:
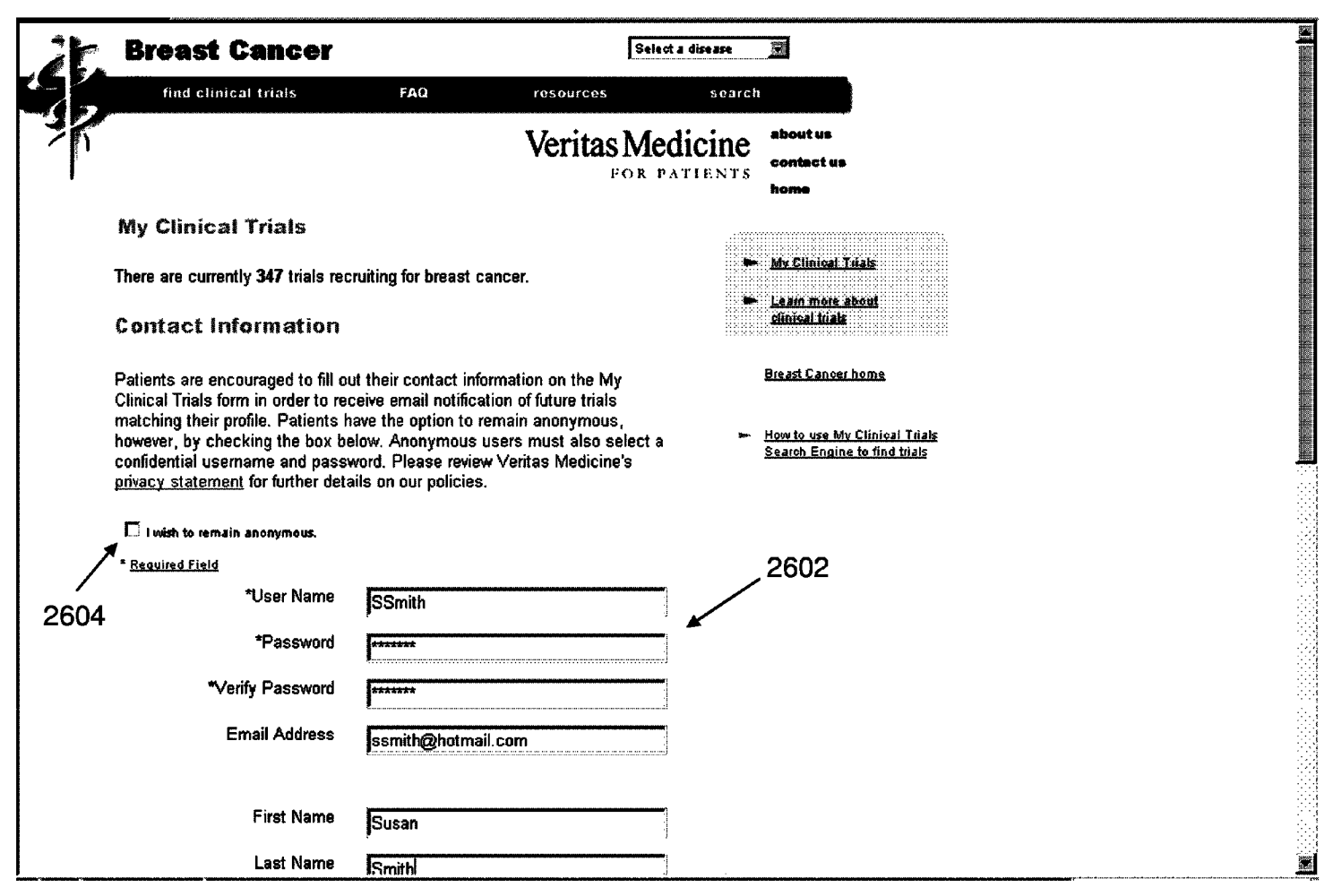

With reference to FIG. 26, patient contact information 2602 may be requested. The patient may alternatively elect to remain anonymous, such as by marking a check-box 2604.

Level 1 questions can be used as an initial filter for patients. Patients enter information including disease of concern, age, and gender, such as shown for lung cancer in FIG. 4.

Figure 27:
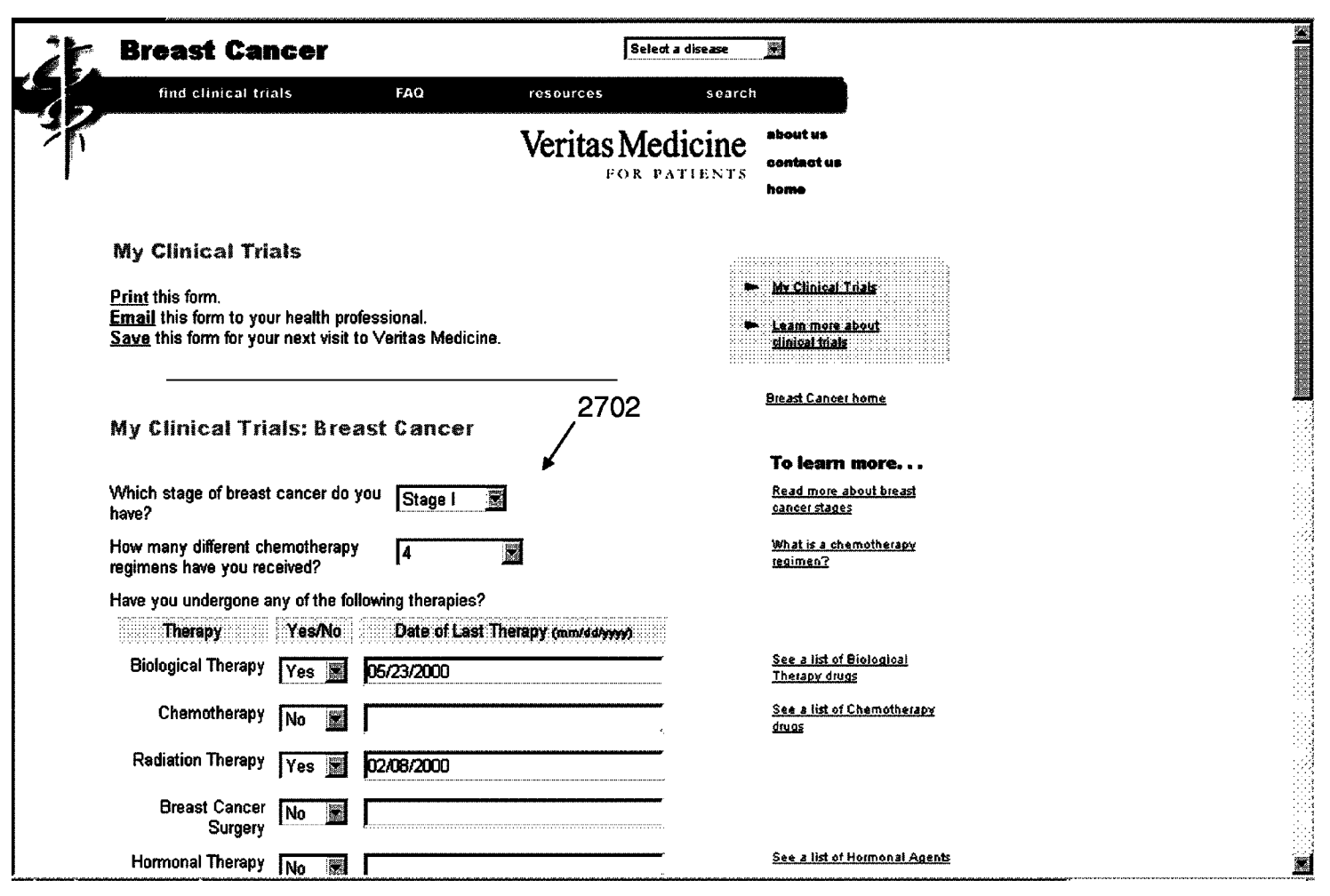

With reference to FIG. 27, the level 2 questions can be determined from the answers given in level 1. These questions are more detail-oriented and disease-specific. Patients may enter information including drug classes of interest, prior therapies, specific drugs of interest, years since diagnosis, stage of disease, phase of clinical trial, other known diseases or infections, and various physiological, biochemical, and pathological parameters applicable to the disease of concern. FIG. 27 illustrates one embodiment of the patient interface displaying a portion 2702 of the level 2 questions that may be presented for Breast Cancer.

In an embodiment, once the match results are sanitized by the security application, the appropriate match results are displayed to the patient. For non-proprietary trials, details such as contact information (i.e., name, phone number, and email address), trial description, trial location, drugs being tested, and eligibility criteria are displayed. For proprietary trials, unless otherwise specified, patients are only shown the trial contact information. All confidential proprietary trial details are hidden and are not accessible via the web. FIG. 28 illustrates one embodiment of the patient interface displaying a portion 2802 of the match results that may be presented for Breast Cancer.

An embodiment comprises a security application layer to allow patients to be matched with appropriate clinical trials while ensuring proprietary trial information is hidden. A secure database system protects sensitive pharmaceutical information (e.g., trial site locations, drugs in development, and trial eligibility criteria) while allowing trials to be matched to appropriate patients.

Figure 29:
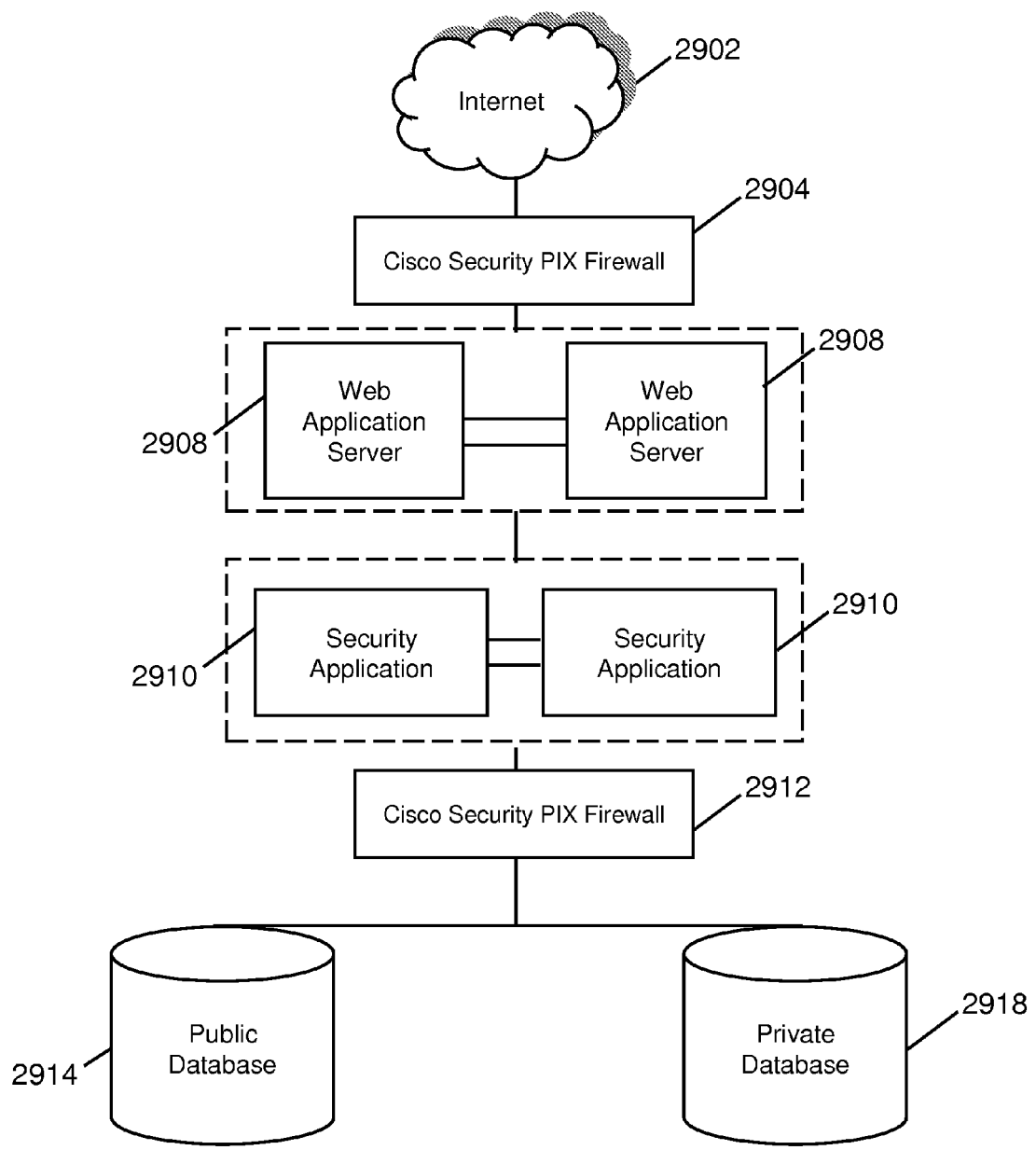
FIG. 29 depicts an exemplary network architecture.

With reference to FIG. 29, a secure network architecture may include a network 2902, an external firewall 2904, a plurality of web application servers 2908, a plurality of security applications 2910, an internal firewall 2912, a public database 2914, and a private database 2918. The equipment making up these elements may include Sun Microsystems enterprise servers; Cisco firewalls, switches and routers; Oracle 8i Enterprise database server; Cold Fusion web application servers; and an Apache web server.

Although it is extremely unlikely that the public servers 2908 ("WWW") will be compromised, the architecture is designed to minimize the damage that can occur in the unlikely event of a breach. The architecture features security applications, multi-tiered arrangement, multiple firewalls, security reinforcement at the database level, off-line loading process for private trial data, fine-grained access control, and Secure Socket Layer encryption.

In an embodiment, a security application 2910 allows for extremely fine-grained control over the data escaping the database and provides an extra layer of network security that a hacker must penetrate before gaining access to valuable trial and patient data. Login alerts on the security application are set up to alert a system administrator to a penetration as it happens. The alerts, in the form of e.g. a page, will allow the administrator to immediately detect the occurrence of unauthorized shell start-ups.

The security application 2910 can be database-based. A small data-caching database can be set up on the security application server. This database can be pushed, using rules programmed and contained on the database, with only the sanitized data that is allowed onto the web page.

In an embodiment, the network architecture is multi-tiered to ensure that private trial and patient data is completely inaccessible from the World Wide Web. All requests submitted to the databases must successfully pass through both the web application server layer 2908 and the security application layer 2910. In addition, two distinct firewalls 2904, 2912 provide additional tiers to further separate private data from the Internet and ensure the system cannot be penetrated.

In an embodiment, multiple firewalls 2904, 2912 are provided. A firewall can control network services both in and out of a network. A perimeter firewall provides several types of protection, including: limiting public users to accepted network traffic; controlling Virtual Private Network (VPN) services from authorized client machines (i.e. experts' machines within an office); and protecting the data center network from many Denial of Service attacks.

The network architecture, as depicted in FIG. 29, allows for a firewall 2912 to be placed in proximity to the private database 2918. Firewall 2912 can protect the private database 2918 from unauthorized access from machines trusted by the perimeter firewall. All other machines within proximity to the private database 2918 and machines connected to the data center network via VPN classify as machines trusted by the primary firewall 2904. The secondary firewall 2912 will control which content managers have access to the private data and which data center machines can request private data. The firewall automatically flags inappropriate requests from unauthorized machines.

In an embodiment, data leaving the database is carefully monitored to ensure that valuable data cannot escape. This restrictive data security policy can frustrate most attempts to obtain private data without authorization. There are two different security levels in the database setup: first, data that is read/write accessible directly from the web; second, highly confidential data is stored separately from the web-accessible data. A very strict security layer allows only specific, predetermined confidential trial information to pass out of the database. All of the medical content and patient data can also be kept behind the security layer.

In an embodiment, a sophisticated matching algorithm compares the patient's data to the clinical trial eligibility data. Matching patient characteristics to both private and public clinical trial eligibility conditions should occur in a secure manner. The bulk of proprietary clinical data should not be passed over to the web side. Instead, only very specific contact information for matching clinical trials should be passed.

In an embodiment, the raw proprietary clinical trial feed received from clinical trial conductors may be held on yet another machine entirely. For maximum security, this machine may not even be on a network. From this "off-line" machine, a first pass of data cleaning and sanitization can be done. Then, data can be loaded into the proprietary database via a "sneaker-net" (e.g. tape, floppy, Zip disk, or CD-Rom), further minimizing the chances of that highly valuable data escaping the organization.

In an embodiment, data scavenging can be thwarted by a harm-reduction security layer on the database itself. The security application protocol is designed to accept requests from particular machines (e.g., the web server wants a patient to clinical trial match) and validate those requests against a short list of acceptable choices (e.g., the web server is asking for one patient's match results, rather than the entire clinical trial data set). Then, the application passes this validated request on to the appropriate database (public, private or both) and assembles an appropriate answer for the web server's question.

In an embodiment, the system may throttle the amount and type of data available to the web application. Without row-level security, the web application might otherwise have to be granted full select (and/or insert, update and delete) access to the database. The web application itself should guarantee that each customer is his or herself, and the web application is responsible for asking the database for only the appropriate customer rows. If the web application is compromised or subverted in a manner that allowed the privileged web application entity to ask for the entire customer table, confidential customer data could be scavenged in its entirety.

Fortunately, row-level security allows the server to enforce throttling rules about how much data the web application can ask for at any one time. For patient data access, the database may allow only a single patient row to be returned by any one query. In order for the malicious competitor to scavenge all the valuable data, they would have to call similar URLs repeatedly, giving the web application security and abuse procedures time to identify the single IP-address querying for each customer record in turn, and shut out the offender. Not only does this policy gain the administrators' valuable time by preventing the wholesale harvesting of data, it also requires the hacker to know individual-specific login names to retrieve any data.

In an embodiment, the server gathers sensitive information about patients and matches against ongoing clinical trials. Private patient data may travel over the public Internet. To ensure patient confidentiality, the web session can be encrypted via 128-bit Secure Socket Layer (SSL) enabled web servers and browsers.

Figure 30:
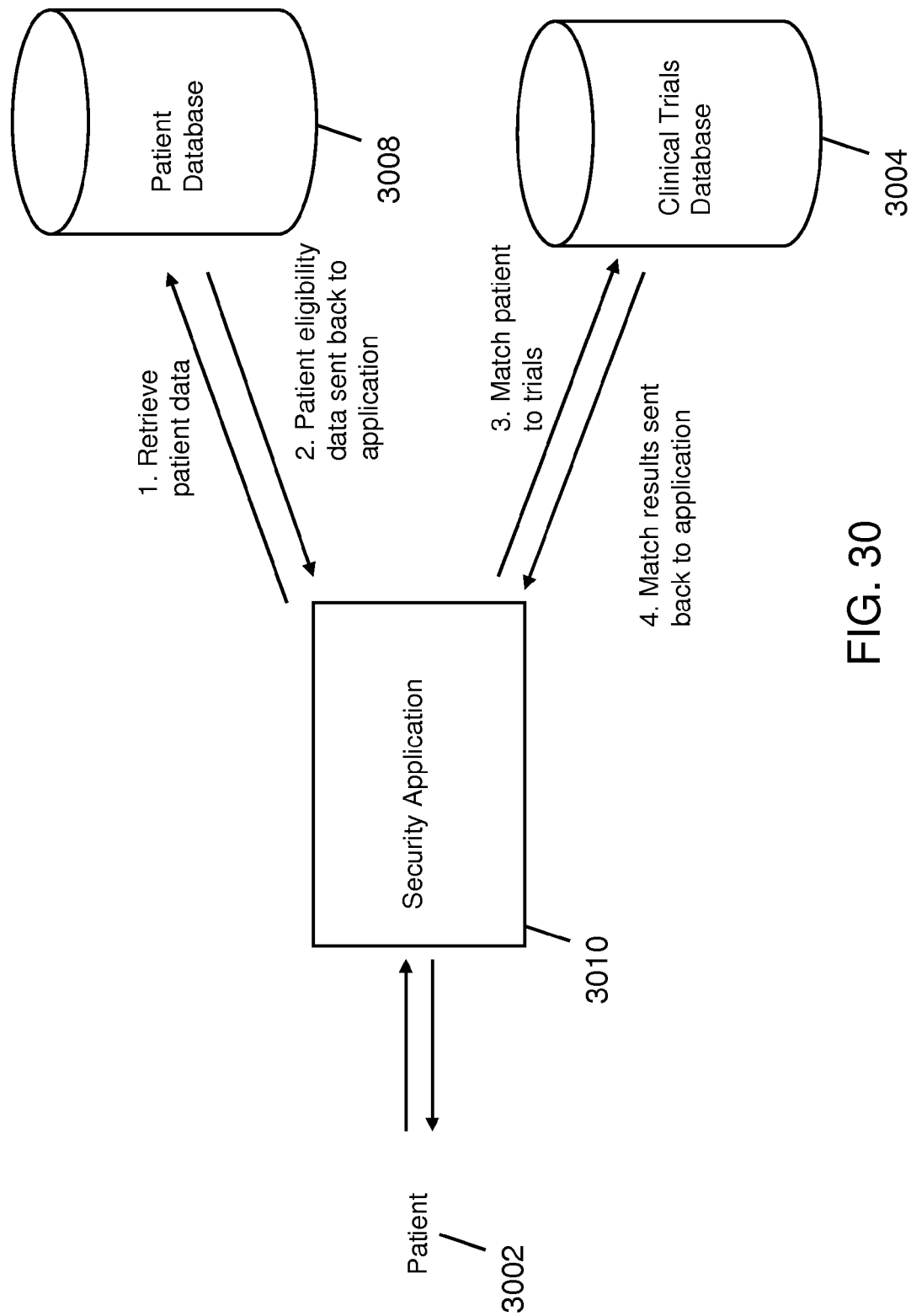
FIG. 30 depicts exemplary secure data flow.

In an embodiment, depicted in FIG. 30, the flow of data to and from the security application is handled as follows:
1. Patient 3002 submits patient-specific data
2. Web server (not shown) requests a trial match
3. Security application 3010 asks patient database for patient data
4. Patient data sent to security application 3010
5. Security application 3010 asks trials database 3004 for a trial match
6. Match results returned to the security application 3010
7. Match results sent to Web server
8. HTML generated
9. Match results displayed on the patient's PC The security application layer 3010 of the network allows the components of the system to remain autonomous. The trials database 3004 is maintained separately from the patient database 3008, and the security application 3010 monitors all protocols that are sent back and forth to the databases 3004, 3008. The security application 3010 sends only the data necessary for trial matching, a patient's eligibility criteria, to the trials database 3004. Patient demographic data (e.g. name, address, and email) is not used in the matching algorithm.

In an embodiment, the security application layer also sanitizes the information passed on to the client system. For non-proprietary trials, details such as contact information (i.e., name, phone number, and email address), trial description, trial location, drugs being tested, and eligibility criteria are displayed. For proprietary trials, unless otherwise specified, the security protocols ensure that all confidential, proprietary trial details are hidden. Only trial contact information is displayed on the web.

An embodiment includes an independent database where pharmaceutical companies can post trials in order to facilitate trial recruitment. The system can serve as an independent third-party hub for proprietary trial data. As a third party, the system can create a marketplace that is structurally impossible for pharmaceutical companies, contract research organizations (CROS) and individual health portals to build. The system offers the necessary components of a trials marketplace: comprehensiveness, lack of bias (e.g., no 'selling' of particular trials), and transparency of market operation.

Pharmaceutical companies can submit trial data to the Clinical Trial Patient Recruitment system by several methods, including: uploading a batch of trial data is into the trials database; or submitting trials one-by-one via a web interface.

Upon submission of a trial, the trial is associated with the desired matching percentage for use in the rules-based matching algorithm. The matching percentage can be site-specific or centralized. Also, upon submission, the appropriate questions are associated with the trial's eligibility criteria.

An embodiment includes a patient database that pharmaceutical companies can access to accelerate patient recruitment. Such a patient database can accelerate patient recruitment with an enhanced probability of attaining an appropriate patient population. A pharmaceutical company can access the patient database to pre-enroll patients into clinical trials. Access to the patient database can accelerate patient recruitment and enhance the probability of attaining an appropriate patient population for a specific trial.

In an embodiment, patients have the option of voluntarily sharing their data with pharmaceutical companies in order to receive information about upcoming trials and relevant treatments. As patients register with the system, they may be added to a database of patients who are interested in entering clinical trials. This facilitates fuller enrollment in clinical trials prior to initiation. This database may become increasingly important as the fields of combinatorial chemistry and genomics spawn thousands of new drug candidates in the near future.

In an embodiment, physicians may access the system to identify trials that may be of interest to their patient or to identify trials that might benefit from opening a new trial location in the vicinity of the physician's office.

In an embodiment, clinical trials may transmit back to the server data concerning patients that have been enrolled in the trial as a result of having matched using the techniques described herein.

In an embodiment, the server can notify patients when new clinical trials become available to which the patients are likely to match, as determined by patient-specific data retained in the patient database.

The techniques described herein are not limited to any particular hardware or software configuration; they may find applicability in any computing or processing environment. The techniques may be implemented in hardware or software, or a combination of the two. Preferably, the techniques are implemented in computer programs executing on programmable computers that each include a processor, a storage medium readable by the processor (including volatile and non-volatile memory and/or storage elements), at least one input device, and one or more output devices.

Each program is preferably implemented in high level procedural or object oriented programming language to communicate with a computer system. However, the programs can be implemented in assembly or machine language, if desired. In any case the language may be compiled or interpreted language.

Each such computer program is preferably stored on a storage medium or device (e.g., CD-ROM, hard disk, or magnetic disk) that is readable by a general or special purpose programmable computer for configuring and operating the computer when the storage medium or device is read by the computer to perform the procedures described herein. The system may also be considered to be implemented as a computer-readable storage medium, configured with a computer program, where the storage medium so configured causes a computer to operate in a specific and predefined manner.

Various alternative embodiments are envisioned and within the scope of the claims. While the subject matter has been particularly shown and described with reference to a number of embodiments thereof, it will be understood by those skilled in the art that various changes in form and details may be made therein without departing from the spirit and scope of the subject matter.

Having disclosed the foregoing subject matter and embodiments thereof, what is claimed as new and secured by Letters Patent is:

1. A method of recruiting a patient into a clinical trial, the method comprising:
   serving from a server to the patient a questionnaire that includes at least one clinical trial eligibility question;
   receiving at the server from the patient patient-specific data that includes an answer to the at least one clinical trial eligibility question, the patient-specific data comprising at least one of: disease of concern, demographic data, drug classes of interest, prior therapies, specific drugs of interest, years since diagnosis, stage of disease, phase of clinical trial, and concomitant diseases;
   sending the patient-specific data from the server to a security layer;
   sending the patient-specific data from the security layer to a matcher;
   preventing direct communication between the server and the matcher;
   accessing criteria of one or more clinical trials;
   determining using the matcher whether the patient-specific data satisfies the criteria of one or more clinical trials, thereby generating match result data in the matcher;
   sending match result data from the matcher to the security layer;
   in the security layer, removing proprietary trial information from the match result data, thereby generating sanitized match result data;
   sending the sanitized match result data to the patient;
   inviting the patient to participate in a clinical trial for which the criteria have been determined to be satisfied, if any; and
   if the patient chooses to participate, registering the patient in a database.

2. A computer system for recruiting a patient into a clinical trial, the system comprising:
   at least one processor programmed with at least a server application, a matcher application, and a security layer, wherein:
   the server application, the matcher application, and the security layer are embodied on a non-transitory computer-readable medium; and
   the server application is configured to:
      request patient-specific data from the patient, the patient-specific data requested including clinical trial eligibility data that comprises at least one of: disease of concern, demographic data, drug classes of interest, prior therapies, specific drugs of interest, years since diagnosis, stage of disease, phase of clinical trial, and concomitant diseases;
      collect the patient-specific data from the patient; and
      send match result data to the patient;

the matcher application is configured to be responsive to the patient's clinical trial eligibility data and to trial-specific criteria corresponding to the clinical trial to:
  determine whether a match exists between the patient and the clinical trial; and
  generate the match result data; and
the security layer is configured to:
  prevent direct communication between the server and the matcher;
  receive the patient-specific data from the server;
  send the patient's clinical trial eligibility data to the matcher; and
  receive the match result data from the matcher;
  remove proprietary trial information from the match result data, thereby generating sanitized match result data; and
  send the sanitized match result data to the server.

3. The system of claim 2, wherein the server communicates with the patient through a patient interface that comprises an HTML-encoded web page.

4. The system of claim 2, further comprising a patient database in which the patient-specific data is stored.

5. The system of claim 4, wherein the security layer is so configured as to send the patient-specific data to the patient database for storage.

6. The system of claim 5, wherein the security layer sends the patient-specific data to the patient database for storage only after the system determines whether a match exists between the patient and the clinical trial.

7. The system of claim 2, further comprising a clinical trial database, in which the set of trial-specific criteria is stored.

8. The system of claim 2, wherein the patient-specific data comprises answers to a questionnaire.

9. The system of claim 2, further configured to send at least a portion of the patient-specific data to the clinical trial.

10. The system of claim 2, wherein the match result data comprises at least one of clinical trial contact and location information, and the 11. The system of claim 2, wherein the system comprises at least two computers.

12. The system of claim 11, wherein the security layer runs on one of the computers, and the matcher runs on another computer.

13. The system of claim 2, wherein the security layer sends the patient's clinical trial eligibility data, but not other patient-specific data, to the matcher.

14. A method of determining whether a patient is a candidate for a clinical trial, comprising:
  serving a questionnaire from a server to a patient through a patient interface;
  receiving at the server patient eligibility data submitted by the patient in response to the questionnaire, the patient eligibility data comprising at least one of: disease of concern, demographic data, drug classes of interest, prior therapies, specific drugs of interest, years since diagnosis, stage of disease, phase of clinical trial, and concomitant diseases;
  sending the patient eligibility data from the server to a security layer;
  sending the patient eligibility data from the security layer to a matcher;
  in the matcher:
    determining whether a match exists between the patient and the clinical trial by comparing the patient eligibility data to a set of trial criteria specific for the clinical trial; and
    returning match result information to the security layer;
  in the security layer, removing proprietary trial information from the match result information, thereby generating sanitized match result information;
  sending to the server the sanitized match result information thus returned from the security layer; and
  serving to the patient through the patient interface the sanitized match result information thus sent to the server.

15. The method of claim 14, further comprising serving at least one of clinical trial contact and location information to the patient through the patient interface.

16. The method of claim 14, further comprising serving a registration questionnaire to the patient through the patient interface after a match has been determined to exist between the patient and the clinical trial.

17. The method of claim 16, further comprising receiving a set of registration information from the patient.

18. The method of claim 17, further comprising adding the registration information to a patient database.

19. The method of claim 17, further comprising sending at least part of the set of registration information to the clinical trial.

20. The method of claim 14, further comprising comparing, in the matcher, the patient eligibility data to a second set of trial criteria and determining whether a match continues to exist between the patient and the clinical trial.

21. The method of claim 14, wherein the security layer and the matcher run on separate computers.

22. A method of determining whether a patient is a candidate for a clinical trial, comprising:
  serving a first questionnaire from a server to a patient through a patient interface;
  receiving at the server a first set of patient eligibility data submitted by the patient in response to the first questionnaire, the first set of patient eligibility data comprising at least one of: disease of concern, demographic data, drug classes of interest, prior therapies, specific drugs of interest, years since diagnosis, stage of disease, phase of clinical trial, and concomitant diseases;
  sending the first set of patient eligibility data from the server to a security layer;
  sending the first set of patient eligibility data from the security layer to a matcher;
  in the matcher:
    determining whether a match exists between the patient and the plurality of clinical trials by comparing the first set of patient eligibility data to a set of generic trial criteria generic to a plurality of clinical trials; and
    returning generic match result information to the security layer;
  if a match exists between the patient and the plurality of clinical trials:
    serving a second questionnaire from the server to the patient through the patient interface;
    receiving at the server a second set of patient eligibility data submitted by the patient in response to the second questionnaire, the second set of patient eligibility data being different from the first set of patient eligibility data and comprising at least one of: disease of concern, demographic data, drug classes of interest, prior therapies, specific drugs of interest, years since diagnosis, stage of disease, phase of clinical trial, and concomitant diseases;
    sending the second set of patient eligibility data from the server to the security layer;
    sending the second set of patient eligibility data from the security layer to the matcher;

in the matcher:
   determining whether a match exists between the patient and the one clinical trial by comparing the second set of patient eligibility data to a set of specific trial criteria specific to one of the plurality of clinical trials; and
   returning specific match result information to the security layer;
if a match exists between the patient and the one clinical trial:
   in the security layer, removing proprietary trial information from the specific match result information, thereby generating sanitized specific match result information;
   sending the sanitized specific match result information from the security layer to the server; and
   serving the sanitized specific match result information to the patient through the patient interface.

* * * * *

UNITED STATES PATENT AND TRADEMARK OFFICE
CERTIFICATE OF CORRECTION

| | | |
|---|---|---|
| PATENT NO. | : 7,904,313 B2 | Page 1 of 1 |
| APPLICATION NO. | : 09/938295 | |
| DATED | : March 8, 2011 | |
| INVENTOR(S) | : Stephen C. Knight | |

It is certified that error appears in the above-identified patent and that said Letters Patent is hereby corrected as shown below:

IN THE SPECIFICATIONS:
    Col. 7, line 47: delete the duplicate word "specific" after "trial-specific"

IN THE CLAIMS:
    Col. 15, line 38, claim 10: insert after "and the" the words --server is configured to send the match result data to the patient.--

Signed and Sealed this
Fifth Day of April, 2011

David J. Kappos
*Director of the United States Patent and Trademark Office*